(12) United States Patent
Daube et al.

(10) Patent No.: US 8,658,153 B2
(45) Date of Patent: Feb. 25, 2014

(54) BIFIDOBACTERIAL SPECIES

(75) Inventors: Georges Daube, Stembert (BE);
Christine Franssen, Verviers (BE);
Véronique Delcenserie, Mississauga (CA); Françoise Gavini, Mons en Bareoul (FR); Bruno Pot, Sint-Michiels Brugge (BE)

(73) Assignees: Universite de Liege, Angleur (BE);
Institut Pasteur de Lille, Lille (BE)

( * ) Notice: Subject to any disclaimer, the term of this patent is extended or adjusted under 35 U.S.C. 154(b) by 159 days.

(21) Appl. No.: 12/734,238

(22) PCT Filed: Jul. 2, 2008

(86) PCT No.: PCT/EP2008/058490
§ 371 (c)(1),
(2), (4) Date: Apr. 20, 2010

(87) PCT Pub. No.: WO2009/049932
PCT Pub. Date: Apr. 23, 2009

(65) Prior Publication Data
US 2010/0310513 A1 Dec. 9, 2010

(30) Foreign Application Priority Data
Oct. 20, 2007 (EP) .................................... 07118938

(51) Int. Cl.
*A61K 35/74* (2006.01)
(52) U.S. Cl.
USPC .................................... 424/93.2; 435/252.1
(58) Field of Classification Search
USPC ..................................................... 435/252.1
See application file for complete search history.

(56) References Cited

FOREIGN PATENT DOCUMENTS

WO   WO 2006/122850   11/2006

OTHER PUBLICATIONS

Simpson P. J et al. "*Bifidobacterium psychraerophilum* sp. nov. and *Aeriscardovia aeriphila* gen. nov. , sp. Nov. , isolated form a porcine caecum" in*International Journal of Systematic and Evolutionary Microbiology*, Society for general microbiology, reading, GB, vol. 54, no Part 2,Mar. 1, 2004, pp. 401-406.
Database EMBL—Jan. 22, 2003, "*Bifidobacterium psychroaerophilum* 16S ribosomal RNA gene, partial sequence", Database accession No. AY174108.
Jian W et al.: "New approach to phylogenetic analysis of the Genus *Bifidobacterium* based on partial HSP60 gene sequences" in *International journal of systematic and evolutionary microbiology*, vol. 51, Sep. 1, 2001, pp. 1633-1638.
Biavati B. et al. "Bifidobacteria: history, ecology, physiology and applications" in*Annals of microbiology*, vol. 50, 2000, pp. 117-131.
Dong et al. "*Bifidobacterium thermacidophilum* sp. nov., isolated from an anaerobic digester" in *International Journal of Systematic and Evolutionary Microbiology*, vol. 50 (2000), pp. 119-125.
Delcenserie V. et al.: "Description of a new species, *Bifidobacterium crudilactis* sp. nov., isolated from raw milk and raw milk cheeses" in*Systematic and Applied Microbiology*, vol. 30 (2007), pp. 381-389.
De Ley et al. "The quantitative measurement ofDNA hybridization from renaturation rates" In Eur. *J Biochem*, vol. 12 (1970), pp. 133-142.
Francoise Gavini et al. "Differences in the Distribution of Bifidobacterial and Enterobacterial Species in Human Faecal Microflora of Three Different (Children, Adults, Elderly) Age Groups" in *Microbial Ecology in Health and Disease*, 1651-2235, vol. 13, Issue 1,2001, pp. 40-45.
Wallace et al. "Inhibition of leukotriene synthesis markedly enhances healing in an animal model of inflammatory bowel disease" In*Gastroenterology*, vol. 96 (1), 1989, pp. 29-36.
Bradley et al. "Measurement of cutaneous inflammation: estimation of neutrophil content with an enzyme marker" in*The Journal of Investigative Dermatology* vol. 78(3), 1982, pp. 206-209.

*Primary Examiner* — Jon P Weber
*Assistant Examiner* — Robert Yamasaki
(74) *Attorney, Agent, or Firm* — Jacobson Holman PLLC

(57) ABSTRACT

New bacterium GC61 belonging to the genus *Bifidobacterium*, probiotic compositions comprising said bacterium, particularly food products, and use of said bacterium in the treatment of diseases, such as gastrointestinal diseases.

7 Claims, 26 Drawing Sheets

Figure 2B:
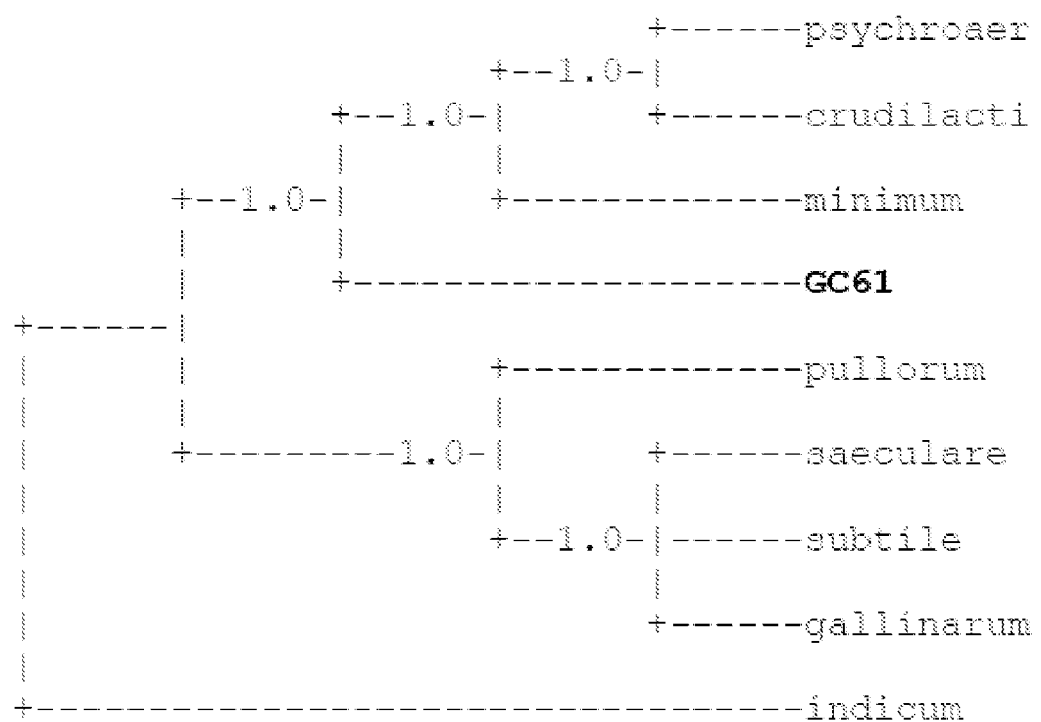

```
1 = FR101/h/8          1473   1 to 1473
2 = FR41/2             1473   1 to 1473
3 = FR49/f/2           1473   1 to 1473
C = consensus 10        20        30        40        50        60
   1  ATCCTGGCTCAGGATGAACGCTGGCGGCGTGCTTAACACATGCAAGTCGAACGGGATCCG
60
   2  -----GGCTCAGGATGAACGCTGGCGGCGTGCTTAACACATGCAAGTCGAACGGGATCCG
55
   3  ------GCTCAGGATGAACGCTGGCGGCGTGCTTAACACATGCAAGTCGAACGGGATCCG
54
   C  .....+GCTCAGGATGAACGCTGGCGGCGTGCTTAACACATGCAAGTCGAACGGGATCCG 70        80        90       100       110       120
   1  AGGCGCTTGCGTCTCGGTGAGAGTGGCGAACGGGTGAGTAATACGTGACTAACCTGCCTC
120
   2  AGGCGCTTGCGTCTCGGTGAGAGTGGCGAACGGGTGAGTAATACGTGACTAACCTGCCTC
115
   3  AGGCGCTTGCGTCTCGGTGAGAGTGGCGAACGGGTGAGTAATACGTGACTAACCTGCCTC
114
   C  AGGCGCTTGCGTCTCGGTGAGAGTGGCGAACGGGTGAGTAATACGTGACTAACCTGCCTC 130       140       150       160       170       180
   1  ATACATCGGAATAGCTCCTGGAAACGGGTGGTAATGCCGAATGCTCCAACCTTCCGCATG
180
   2  ATACATCGGAATAGCTCCTGGAAACGGGTGGTAATGCCGAATGCTCCAACCTTCCGCATG
175
   3  ATACATCGGAATAGCTCCTGGAAACGGGTGGTAATGCCGAATGCTCCAACCTTCCGCATG
174
   C  ATACATCGGAATAGCTCCTGGAAACGGGTGGTAATGCCGAATGCTCCAACCTTCCGCATG 190       200       210       220       230       240
   1  GATGGTTGGGAAAGCGTTAGCGGTATGAGATGGGGTCGCGTCCTATCAGCTTGTTGGTGG
240
   2  GATGGTTGGGAAAGCGTTAGCGGTATGAGATGGGGTCGCGTCCTATCAGCTTGTTGGTGG
235
   3  GATGGTTGGGAAAGCGTTAGCGGTATGAGATGGGGTCGCGTCCTATCAGCTTGTTGGTGG
234
   C  GATGGTTGGGAAAGCGTTAGCGGTATGAGATGGGGTCGCGTCCTATCAGCTTGTTGGTGG
```

Figure 1A...

```
              250        260        270        280        290        300
     1  GGTGAAGGCCCACCAAGGCTTCGACGGGTAGCCGGCCTGAGAGGGTGACCGGCCACATTG
  300
     2  GGTGAAGGCCCACCAAGGCTTCGACGGGTAGCCGGCCTGAGAGGGTGACCGGCCACATTG
  295
     3  GGTGAAGGCCCACCAAGGCTTCGACGGGTAGCCGGCCTGAGAGGGTGACCGGCCACATTG
  294
     C  GGTGAAGGCCCACCAAGGCTTCGACGGGTAGCCGGCCTGAGAGGGTGACCGGCCACATTG 310        320        330        340        350        360
     1  GGACTGAGATACGGCCCAGACTCCTACGGGAGGCAGCAGTGGGGAATATTGCACAATGGG
  360
     2  GGACTGAGATACGGCCCAGACTCCTACGGGAGGCAGCAGTGGGGAATATTGCACAATGGG
  355
     3  GGACTGAGATACGGCCCAGACTCCTACGGGAGGCAGCAGTGGGGAATATTGCACAATGGG
  354
     C  GGACTGAGATACGGCCCAGACTCCTACGGGAGGCAGCAGTGGGGAATATTGCACAATGGG 370        380        390        400        410        420
     1  CGAAAGCCTGATGCAGCGACGCCGCGTGCGGGATGAAGGCCTTCGGGTTGTAAACCGCTT
  420
     2  CGAAAGCCTGATGCAGCGACGCCGCGTGCGGGATGAAGGCCTTCGGGTTGTAAACCGCTT
  415
     3  CGAAAGCCTGATGCAGCGACGCCGCGTGCGGGATGAAGGCCTTCGGGTTGTAAACCGCTT
  414
     C  CGAAAGCCTGATGCAGCGACGCCGCGTGCGGGATGAAGGCCTTCGGGTTGTAAACCGCTT 430        440        450        460        470        480
     1  TTGATTGGGAGCAAGCGAGAGTGAGTGTACCTTTCGAATAAGCACCGGCTAACTACGTGC
  480
     2  TTGATTGGGAGCAAGCGAGAGTGAGTGTACCTTTCGAATAAGCACCGGCTAACTACGTGC
  475
     3  TTGATTGGGAGCAAGCGAGAGTGAGTGTACCTTTCGAATAAGCACCGGCTAACTACGTGC
  474
     C  TTGATTGGGAGCAAGCGAGAGTGAGTGTACCTTTCGAATAAGCACCGGCTAACTACGTGC
```

Figure 1A continued...

```
              490       500       510       520       530       540
     1    CAGCAGCCGCGGTAATACGTAGGGTGCAAGCGTTATCCGGAATTATTGGGCGTAAAGAGC
540
     2    CAGCAGCCGCGGTAATACGTAGGGTGCAAGCGTTATCCGGAATTATTGGGCGTAAAGAGC
535
     3    CAGCAGCCGCGGTAATACGTAGGGTGCAAGCGTTATCCGGAATTATTGGGCGTAAAGAGC
534
     C    CAGCAGCCGCGGTAATACGTAGGGTGCAAGCGTTATCCGGAATTATTGGGCGTAAAGAGC 550       560       570       580       590       600
     1    TCGTAGGCGGTTTGTCGCGTCTGGTGTGAAAGTCCATCGCTTAACGGTGGATCTGCGCCG
600
     2    TCGTAGGCGGTTTGTCGCGTCTGGTGTGAAAGTCCATCGCTTAACGGTGGATCTGCGCCG
595
     3    TCGTAGGCGGTTTGTCGCGTCTGGTGTGAAAGTCCATCGCTTAACGGTGGATCTGCGCCG
594
     C    TCGTAGGCGGTTTGTCGCGTCTGGTGTGAAAGTCCATCGCTTAACGGTGGATCTGCGCCG 610       620       630       640       650       660
     1    GGTACGGGCAGGCTAGAGTGCGACAGGGGAGACTGGAATTCCCGGTGTAACGGTGGAATG
660
     2    GGTACGGGCAGGCTAGAGTGCGACAGGGGAGACTGGAATTCCCGGTGTAACGGTGGAATG
655
     3    GGTACGGGCAGGCTAGAGTGCGACAGGGGAGACTGGAATTCCCGGTGTAACGGTGGAATG
654
     C    GGTACGGGCAGGCTAGAGTGCGACAGGGGAGACTGGAATTCCCGGTGTAACGGTGGAATG 670       680       690       700       710       720
     1    TGTAGATATCGGGAAGAACACCAATGGCGAAGGCAGGTCTCTGGGTCGTCACTGACGCTG
720
     2    TGTAGATATCGGGAAGAACACCAATGGCGAAGGCAGGTCTCTGGGTCGTCACTGACGCTG
715
     3    TGTAGATATCGGGAAGAACACCAATGGCGAAGGCAGGTCTCTGGGTCGTCACTGACGCTG
714
     C    TGTAGATATCGGGAAGAACACCAATGGCGAAGGCAGGTCTCTGGGTCGTCACTGACGCTG 730       740       750       760       770       780
     1    AGGAGCGAAAGCGTGGGGAGCGAACAGGATTAGATACCCTGGTAGTCCACGCCGTAAACG
780
     2    AGGAGCGAAAGCGTGGGGAGCGAACAGGATTAGATACCCTGGTAGTCCACGCCGTAAACG
775
     3    AGGAGCGAAAGCGTGGGGAGCGAACAGGATTAGATACCCTGGTAGTCCACGCCGTAAACG
774
     C    AGGAGCGAAAGCGTGGGGAGCGAACAGGATTAGATACCCTGGTAGTCCACGCCGTAAACG
```

Figure 1A continued...

```
                  790        800        810        820        830        840
        1   GTGGATGCTGGATGTGGGGCCCATTCCACGGGTTCCGTGTCGGAGCTAACGCGTTAAGCA
840
        2   GTGGATGCTGGATGTGGGGCCCATTCCACGGGTTCCGTGTCGGAGCTAACGCGTTAAGCA
835
        3   GTGGATGCTGGATGTGGGGCCCATTCCACGGGTTCCGTGTCGGAGCTAACGCGTTAAGCA
834
        C   GTGGATGCTGGATGTGGGGCCCATTCCACGGGTTCCGTGTCGGAGCTAACGCGTTAAGCA 850        860        870        880        890        900
        1   TCCCGCCTGGGGAGTACGGCCGCAAGGCTAAAACTCAAAGAAATTGACGGGGGCCCGCAC
900
        2   TCCCGCCTGGGGAGTACGGCCGCAAGGCTAAAACTCAAAGAAATTGACGGGGGCCCGCAC
895
        3   TCCCGCCTGGGGAGTACGGCCGCAAGGCTAAAACTCAAAGAAATTGACGGGGGCCCGCAC
894
        C   TCCCGCCTGGGGAGTACGGCCGCAAGGCTAAAACTCAAAGAAATTGACGGGGGCCCGCAC 910        920        930        940        950        960
        1   AAGCGGCGGAGCATGCGGATTAATTCGATGCAACGCGAAGAACCTTACCTGGGCTTGACA
960
        2   AAGCGGCGGAGCATGCGGATTAATTCGATGCAACGCGAAGAACCTTACCTGGGCTTGACA
955
        3   AAGCGGCGGAGCATGCGGATTAATTCGATGCAACGCGAAGAACCTTACCTGGGCTTGACA
954
        C   AAGCGGCGGAGCATGCGGATTAATTCGATGCAACGCGAAGAACCTTACCTGGGCTTGACA 970        980        990       1000       1010       1020
        1   TGTTCCTGACGGCCGCGGAGACGCGGCTTCCCTTCGGGGCAGGTTCACAGGTGGTGCATG
1020
        2   TGTTCCTGACGGCCGCGGAGACGCGGCTTCCCTTCGGGGCAGGTTCACAGGTGGTGCATG
1015
        3   TGTTCCTGACGGCCGCGGAGACGCGGCTTCCCTTCGGGGCAGGTTCACAGGTGGTGCATG
1014
        C   TGTTCCTGACGGCCGCGGAGACGCGGCTTCCCTTCGGGGCAGGTTCACAGGTGGTGCATG
```

Figure 1A continued...

```
              1030       1040       1050       1060       1070       1080
    1  GTCGTCGTCAGCTCGTGTCGTGAGATGTTGGGTTAAGTCCCGCAACGAGCGCAACCCTCG
1080
    2  GTCGTCGTCAGCTCGTGTCGTGAGATGTTGGGTTAAGTCCCGCAACGAGCGCAACCCTCG
1075
    3  GTCGTCGTCAGCTCGTGTCGTGAGATGTTGGGTTAAGTCCCGCAACGAGCGCAACCCTCG
1074
    C  GTCGTCGTCAGCTCGTGTCGTGAGATGTTGGGTTAAGTCCCGCAACGAGCGCAACCCTCG 1090       1100       1110       1120       1130       1140
    1  CCTTGTGTTGCCAGCACGTTATGGTGGGAACTCGCAAGGGACCGCCGGGGTTAACTCGGA
1140
    2  CCTTGTGTTGCCAGCACGTTATGGTGGGAACTCGCAAGGGACCGCCGGGGTTAACTCGGA
1135
    3  CCTTGTGTTGCCAGCACGTTATGGTGGGAACTCGCAAGGGACCGCCGGGGTTAACTCGGA
1134
    C  CCTTGTGTTGCCAGCACGTTATGGTGGGAACTCGCAAGGGACCGCCGGGGTTAACTCGGA 1150       1160       1170       1180       1190       1200
    1  GGAAGGTGGGGATGACGTCAGATCATCATGCCCCTTACGTCTAGGGCTTCACGCATGCTA
1200
    2  GGAAGGTGGGGATGACGTCAGATCATCATGCCCCTTACGTCCAGGGCTTCACGCATGCTA
1195
    3  GGAAGGTGGGGATGACGTCAGATCATCATGCCCCTTACGTCTAGGGCTTCACGCATGCTA
1194
    C  GGAAGGTGGGGATGACGTCAGATCATCATGCCCCTTACGTCTAGGGCTTCACGCATGCTA
```

Figure 1A continued...

```
           1210       1220       1230       1240       1250       1260
    1  CAATGGCCGGTACAACGGGATGCGACGCGGTGACGCGGAGCGGATCCCTTAAAACCGGTC
1260
    2  CAATGGCCGGTACAACGGGATGCGACGCGGTGACGCGGAGCGGATCCCTTAAAACCGGTC
1255
    3  CAATGGCCGGTACAACGGGATGCGACGCGGTGACGCGGAGCGGATCCCTTAAAACCGGTC
1254
    C  CAATGGCCGGTACAACGGGATGCGACGCGGTGACGCGGAGCGGATCCCTTAAAACCGGTC 1270       1280       1290       1300       1310       1320
    1  TCAGTTCGGATTGGAGTCTGCAACTCGACTCCATGAAGGCGGAGTCGCTAGTAATCGCGA
1320
    2  TCAGTTCGGATTGGAGTCTGCAACTCGACTCCATGAAGGCGGAGTCGCTAGTAATCGCGA
1315
    3  TCAGTTCGGATTGGAGTCTGCAACTCGACTCCATGAAGGCGGAGTCGCTAGTAATCGCGA
1314
    C  TCAGTTCGGATTGGAGTCTGCAACTCGACTCCATGAAGGCGGAGTCGCTAGTAATCGCGA
```

Figure 1A continued...

```
          1330       1340       1350       1360       1370       1380
  1  ATCAGCAACGTCGCGGTGAATGCGTTCCCGGGCCTTGTACACACCGCCCGTCAAGTCATG
1380
  2  ATCAGCAACGTCGCGGTGAATGCGTTCCCGGGCCTTGTACACACCGCCCGTCAAGTCATG
1375
  3  ATCAGCAACGTCGCGGTGAATGCGTTCCCGGGCCTTGTACACACCGCCCGTCAAGTCATG
1374
  C  ATCAGCAACGTCGCGGTGAATGCGTTCCCGGGCCTTGTACACACCGCCCGTCAAGTCATG 1390       1400       1410       1420       1430       1440
  1  AAAGTGGGTAGCACCCGAAGCCGGTGGCCTAACCTTTTGGGGGAGCCGTCTAAGGTGAG
1440
  2  AAAGTGGGTAGCACCCGAAGCCGGTGGCCTAACCTTTTGGGGGAGCCGTCTAAGGTGAG
1435
  3  AAAGTGGGTAGCACCCGAAGCCGGTGGCCTAACCTTTTGGGGGAGCCGTCTAAGGTGAG
1434
  C  AAAGTGGGTAGCACCCGAAGCCGGTGGCCTAACCTTTTGGGGGAGCCGTCTAAGGTGAG 1450       1460       1470
  1  ACTCGTGATTGGGACTAA-GTCGTAA-CAAGG-
1470
  2  ACTCGTGATTGGGACTAA---------------
1453
  3  ACTCGTGATTGGGACTAAAGTCGTAAACAAGGT
1467
  C  ACTCGTGATTGGGACTAA.+++++++.+++++.
```

Figure 1A continued

```
Bifidobacterium_vercorsense_16s_rRNA_gene
1-
GCTCAGGATGAACGCTGGCGGCGTGCTTAACACATGCAAGTCGAACGGGATCCGAGGCGCTTGCGTC
TCGGTGAGAGTGGCGAACGGGTGAGTAATACGTGACTAACCTGCCTCATACATCGGAATAGCTCCTG
GAAACGGGTGGTAATGCCGAATGCTCCAACCTTCCGCATGGATGGTTGGGAAAGCGTTAGCGGTATG
AGATGGGGTCGCGTCCTATCAGCTTGTTGGTGGGGTGAAGGCCCACCAAGGCTTCGACGGGTAGCCG
GCCTGAGAGGGTGACCGGCCACATTGGGACTGAGATACGGCCCAGACTCCTACGGGAGGCAGCAGTG
GGGAATATTGCACAATGGGCGAAAGCCTGATGCAGCGACGCCGCGTGCGGGATGAAGGCCTTCGGGT
TGTAAACCGCTTTTGATTGGGAGCAAGCGAGAGTGAGTGTACCTTTCGAATAAGCACCGGCTAACTA
CGTGCCAGCAGCCGCGGTAATACGTAGGGTGCAAGCGTTATCCGGAATTATTGGGCGTAAAGAGCTC
GTAGGCGGTTTGTCGCGTCTGGTGTGAAAGTCCATCGCTTAACGGTGGATCTGCGCCGGGTACGGGC
AGGCTAGAGTGCGACAGGGGAGACTGGAATTCCCGGTGTAACGGTGGAATGTGTAGATATCGGGAAG
AACACCAATGGCGAAGGCAGGTCTCTGGGTCGTCACTGACGCTGAGGAGCGAAAGCGTGGGGAGCGA
ACAGGATTAGATACCCTGGTAGTCCACGCCGTAAACGGTGGATGCTGGATGTGGGGCCCATTCCACG
GGTTCCGTGTCGGAGCTAACGCGTTAAGCATCCCGCCTGGGGAGTACGGCCGCAAGGCTAAAACTCA
AAGAAATTGACGGGGGCCCGCACAAGCGGCGGAGCATGCGGATTAATTCGATGCAACGCGAAGAACC
TTACCTGGGCTTGACATGTTCCTGACGGCCGCGGAGACGCGGCTTCCCTTCGGGGCAGGTTCACAGG
TGGTGCATGGTCGTCGTCAGCTCGTGTCGTGAGATGTTGGGTTAAGTCCCGCAACGAGCGCAACCCT
CGCCTTGTGTTGCCAGCACGTTATGGTGGGAACTCGCAAGGGACCGCCGGGGTTAACTCGGAGGAAG
GTGGGGATGACGTCAGATCATCATGCCCCTTACGTCCAGGGCTTCACGCATGCTACAATGGCCGGTA
CAACGGGATGCGACGCGGTGACGCGGAGCGGATCCCTTAAAACCGGTCTCAGTTCGGATTGGAGTCT
GCAACTCGACTCCATGAAGGCGGAGTCGCTAGTAATCGCGAATCAGCAACGTCGCGGTGAATGCGTT
CCCGGGCCTTGTACACACCGCCCGTCAAGTCATGAAAGTGGGTAGCACCCGAAGCCGGTGGCCTAAC
CTTTTGGGGGAGCCGTCTAAGGTGAGACTCGTGATTGGGACTAA
-1452 pb
```

Figure 1B

Figure 2A...

```
1  GC61              1519    1 to 1519
2  psychroaerophilum 1519    1 to 1519
3  subtile           1519    1 to 1519
4  gallinarum        1519    1 to 1519
5  saeculare         1519    1 to 1519
6  pullorum          1519    1 to 1519
7  minimum           1519    1 to 1519
8  crudilactis       1519    1 to 1519
9  indicum           1519    1 to 1519

10        20        30        40        50        60
1  ---------------GCTCAGGATGAACGCTGGCGGCGTGCTTAACACATGCAAGTCGAACG   48
2  ---------------GTCAGGATGAACGCTGGCGGCGTGCTTAACACATGCAAGTCGAACG    46
3  -GTTTCGATTCTGGCTCAGGATGAACGCTGGCGGCGTGCTTAACACATGCAAGTCGAACG    59
4  -----CGATTCTGGCTCAGGATGAACGCTGGCGGCGTGCTTAACACATGCAAGTCGAACG    55
5  ----TTCGATTCTGGCTCAGGATGAACGCTGGCGGCGTGCTTAACACATGCAAGTCGAACG   57
6  GAGTTTGATCATGGCTCAGGATGAACGCTGGCGGCGTGCTTAACACATGCAAGTCGAACG    60
7  --------------------------TGGCGGCGTGCTTA-CACATGCAAGTCGANCG      31
8  ----------------------------------------------------------AG    2
9  ---TTTGATCATGGCTCAGGATGAACGCTGGCGGCGTGCTTAACACATGCAAGTCGAACG    57
C  :.::::..:+++++++++++++++++*******************************G 70        80        90       100       110       120
1  GGATC......GCTTG.......GTGAGAGTGGCGAACGGGTGAGTAAT.CGTGAC.AAC   108
2  GGATC......GCTTG.......GTGAGAGTGGCGAACGGGTGAGTAAT.CGTGAC.AAC   106
3  GGATC......GCTTG.......GTGAGAGTGGCGAACGGGTGAGTAAT.CGTGAC.AAC   119
4  GGATC......GCTTG.......GTGAGAGTGGCGAACGGGTGAGTAAT.CGTGAC.AAC   115
5  GGATC......GCTTG.......GTGAGAGTGGCGAACGGGTGAGTAAT.CGTGAC.AAC   117
6  GGATC......GCTTG.......GTGAGAGTGGCGAACGGGTGAGTAAT.CGTGAC.AAC   120
7  GGATCG....CAAGCTTGCTT..CGTGAGAGTGGCGAACGGGTGAGTAAT.CGTGAC.AAC   91
8  GGATCAT.AA.GCTTGCTT.AT.GTGAGAGTGGCGAACGGGTGAGTAAT.CGTGAC.AAC   62
9  GGATCAT.AA.GCTTGCTT.GT.GTGAGAGTGGCGAACGGGTGAGTAAT.CGTGAC.AAC   117
C  GGATC......GCTTG.:+:+::.TGAGAGTGGCGAACGGGTGAGTAAT.CGTGAC.AAC
```

Figure 2A continued...

```
            310        320        330        340        350        360
1  GCCACATTGGGACTGAGATACGGCCCAGACTCCTACGGGAGGCAGCAGTGGGGAATATTG  346
2  GCCACATTGGGACTGAGATACGGCCCAGACTCCTACGGGAGGCAGCAGTGGGGAATATTG  344
3  GCCACATTGGGACTGAGATACGGCCCAGACTCCTACGGGAGGCAGCAGTGGGGAATATTG  357
4  GCCACATTGGGACTGAGATACGGCCCAGACTCCTACGGGAGGCAGCAGTGGGGAATATTG  353
5  GCCACATTGGGACTGAGATACGGCCCAGACTCCTACGGGAGGCAGCAGTGGGGAATATTG  355
6  GCCACATTGGGACTNAGATACGGCCCAGACTCCTACGGGAGGCAGCAGTGGGGAATATTG  358
7  GCCACATTGGGACTGAGATACGGCCCAGACTCCTACGGGAGGCAGCAGTGGGGAATATTG  329
8  GCCACATTGGGACTGAGATACGGCCCAGACTCCTACGGGAGGCAGCAGTGGGGAATATTG  300
9  GCCACATTGGGACTGAGATACGGCCCAGACTCCTACGGGAGGCAGCAGTGGGGAATATTG  356
C  GCCACATTGGGACT*AGATACGGCCCAGACTCCTACGGGAGGCAGCAGTGGGGAATATTG 370        380        390        400        410        420
1  CGCAATGGGCGAAAGCCTGAGGCAGCGACGCCGCGTGCGGGATGAAGGCCTTCGGGTTGT  406
2  CGCAATGGGCGAAAGCCTGAGGTAGCGACGCCGCGTGCGGGATGAAGGCCTTCGGGTTGT  404
3  CGTAATGGGCGAAAGCCTGAGGCAGCGACGCCGCGTGCGGGATGAAGGCCTTCGGGTTGT  417
4  CGTAATGGGCGAAAGCCTGAGGCAGCGACGCCGCGTGCGGGATGAGGC-TTCGGGTTGT  412
5  CGCAATGGGCGAAAGCCTGAGGTAGCGACGCCGCGTGCGGGATGAAGGCCTTCGGGTTGT  415
6  CGTAATGGGCGAAAGCCTGAGGCAGCGACGCCGCGTGCGGGATGAGGCCTTCGGGTTGT  418
7  CGCAATGGGCGAAAGCCTGAGGTAGCGACGCCGCGTGCGGGATGAAGGCCTTCGGGTTGT  389
8  CGCAATGGGCGAAAGCCTGAGGCAGCGACGCCGCGTGCGGGATGAAGGCCTTCGGGTTGT  360
9  CGCAATGGGCGAAAGCCTGAGGCAGCGACGCCGCGTGCGGGATGACGGCCTTCGGGTTGT  416
C  CGCAATGGGCGAAAGCCTGAGGCAGCGACGCCGCGTGCGGGATGNGGC*TTCGGGTTGT 430        440        450        460        470        480
1  AAACCGCTTTTAAGGGGAGCAAGCGAGAGTGAGTGTACCTTTGAATAAGCACCGGCTA  466
2  AAACCGCTTTTAAGGGGAGCAAGCGAGAGTGAGTGTACCTTTGAATAAGCACCGGCTA  464
3  AAACCGCTTTTATGGGAGCAAGCGAGAGTGAGTGTACCGTGAATAAGCACCGGCTA  477
4  AAACCGCTTTTATGGGAGCAAGCGAGAGTGAGTGTACCTTGAATAAGCACCGGCTA  472
5  AAACCGCTTTTATGGGAGCAAGCGAGAGTGAGTGTACCGTTGAATAAGCACCGGCTA  475
6  AAACCGCTTTTACGGGAGCAAGCGAGAGTGAGTGTACCGTGAATAAGCACCGGCTA  478
7  AAACCGCTTTTGAGGGAGCAAGCGAGAGTGAGTGTACCTTGAATAAGCACCGGCTA  449
8  AAACCGCTTTTAATGGGAGCAAGCGAGAGTGAGTGTACCTTTGAATAAGCACCGGCTA  420
9  AAACCGCTTTTGATGGGAGCAAGCGAGAGTGAGTGTACCGTGAATAAGCACCGGCTA  476
C  AAACCGCTTTTNNNGGGAGCAAGCGAGAGTGAGTGTACCNNTGAATAAGCACCGGCTA 490        500        510        520        530        540
1  ACTACGTGCCAGCAGCCGCGGTAATACGTAGGGTGCAAGCGTTATCCGGATTATTGGGC  526
2  ACTACGTGCCAGCAGCCGCGGTAATACGTAGGGTGCAAGCGTTATCCGGATTATTGGGC  524
3  ACTACGTGCCAGCAGCCGCGGTAATACGTAGGGTGCAAGCGTTATCCGGATTATTGGGC  537
4  ACTACGTGCCAGCAGCCGCGGTAATACGTAGGGTGCAAGCGTTATCCGGATTATTGGGC  532
5  ACTACGTGCCAGCAGCCGCGGTAATACGTAGGGTGCAAGCGTTATCCGGATTATTGGGC  535
6  ACTACGTGCCAGCAGCCGCGGTAATACGTAGGGTGCAAGCGTTATCGGATTATTGGGC  538
7  ACTACGTGCCAGCAGCCGCGGTAATACGTAGGGTGCAAGCGTTATCCGGATTATTGGGC  509
8  ACTACGTGCCAGCAGCCGCGGTAATACGTAGGGTGCAAGCGTTATCCGGATTATTGGGC  480
9  ACTACGTGCCAGCAGCCGCGGTAATACGTAGGGTGCAAGCGTTATCCGGATTATTGGGC  536
C  ACTACGTGCCAGCAGCCGCGGTAATACGTAGGGTGCAAGCGTTATCCGGATTATTGGGC
```

Figure 2A continued...

```
         550        560        570        580        590        600
1  GTAAAGAGCTCGTAGGCGGTTTGTCGCGCTGGTGTGAAAGTCCATCGCTTAACGGTGGA  586
2  GTAAAGAGCTCGTAGGCGGTTTGTCACGCTGGTGTGAAAGTCCATCGCTTAACGGTGGA  584
3  GTAAAGGGCTCGTAGGCGGTTTGTCGCGCTGGTGTGAAAGTCCATCGCTTAACGGTGGA  597
4  GTAAAGGGCTCGTAGGCGGTTTGTCGCGCTGGTGTGAAAGTCCATCGCTTAACGGTGGA  592
5  GTAAAGGGCTCGTAGGCGGTTTGTCGCGCTGGTGTGAAAGTCCATCGCTTAACGGTGGA  595
6  GTAAAGAGCTCGTAGGCGGTTCGTCGCGCTGGTGTGAAAGTCCATCGCTTAACGGTGGA  598
7  GTAAAGAGCTCGTAGGCGGTTTGTCGCGCTGGTGTGAAAGTCCATCGCTTAACGGTGGA  569
8  GTAAAGAGCTCGTAGGCGGTTTGTCACGCTGGTGTGAAAGTCCATCGCTTAACGGTGGA  540
9  GTAAAGAGCTCGTAGGCGGTTCGTCGCGCTGGTGTGAAAGTCCATCGCTTAACGGTGGA  596
C  GTAAAGGGCTCGTAGGCGGTTTGTCGCGCTGGTGTGAAAGTCCATCGCTTAACGGTGGA 610        620        630        640        650        660
1  TCTGCGCCGGGTACGGGCAGGCTAGAGTGCGATAGGGAGACTGGAATTCCCGGTGTAAC  646
2  TCTGCGCCGGGTACGGGCAGGCTAGAGTGCATTAGGGAGACTGGAATTCCCGGTGTAAC  644
3  TCTGCGCCGGGTACGGGCGGGCTAGAGTGCGGCAGGGAGACTGGAATTCCCGGTGTAAC  657
4  TCTGCGCCGGGTACGGGCGGGCTAGAGTGCGGCATGGGAGACTGGAATTCCCGGTGTAAC  652
5  TCTGCGCCGGGTACGGGCGGCTAGAGTGCGGCAGGGAGACTGGAATTCCCGGTGTAAC  655
6  TCTGCGCCGGGTACGGGCGGCTAGAGTGCGGCAGGGAGACTGGAATTCCCGGTGTAAC  658
7  TCTGCGCCGGGTACGGGCAGGCTAGAGTGCAGTAGGGAGACTGGAATTCCCGGTGTAAC  629
8  TCTGCGCCGGGTACGGGCAGGCTAGAGTGCATTAGGGAGACTGGAATTCCCGGTGTAAC  600
9  TCTGCGCCGGGTACGGGCGGACTAGAGTGCGGTAGGGAGACTGGAATTCCCGGTGTAAC  656
C  TCTGCGCCGGGTACGGGCGGCTAGAGTGCGGTAGGGAGACTGGAATTCCCGGTGTAAC 670        680        690        700        710        720
1  GGTGGAATGTGTAGATATCGGGAAGAACACCAATGGCGAAGGCAGTCTCTGGGCGTCA  706
2  GGTGGAATGTGTAGATATCGGGAAGAACACCAATGGCGAAGGCAGTCTCTGGGCGTGA  704
3  GGTGGAATGTGTAGATATCGGGAAGAACACCAATGGCGAAGGCAGTCTCTGGGCGTTA  717
4  GGTGGAATGTGTAGATATCGGGAAGAACACCAATGGCGAAGGCAGTCTCTGGGCGTTA  712
5  GGTGGAATGTGTAGATATCGGGAAGAACACCAATGGCGAAGGCAGTCTCTGGGCGTTA  715
6  GGTGGAATGTGTAGATATCGGGAAGAACACCAATGGCGAAGGCAGTCTCTGGGCGTTA  718
7  GGTGGAATGTGTAGATATCGGGAAGAACACCAATGGCGAAGGCAGTCTCTGGGCGTTA  689
8  GGTGGAATGTGTAGATATCGGGAAGAACACCAATGGCGAAGGCAGTCTCTGGGCGTTA  660
9  GGTGGAATGTGTAGATATCGGGAAGAACACCAATGGCGAAGGCAGTCTCTGGGCGTTA  716
C  GGTGGAATGTGTAGATATCGGGAAGAACACCAATGGCGAAGGCAGTCTCTGGGCGTTA
```

Figure 2A continued...

```
         730       740       750       760       770       780
1   CTGACGCTGAGGAGCGAAAGCTGGGGAGCGAACAGGATTAGATACCCTGGTAGTCCAGG   766
2   CTGACGCTGAGGAGCGAAAGCATGGGGAGCGAACAGGATTAGATACCCTGGTAGTCCAGG  764
3   CTGACGCTGAGGAGCGAAAGCTGGGGAGCGAACAGGATTAGATACCCTGGTAGTCCAGG   777
4   CTGACGCTGAGGAGCGAAAGCTGGGGAGCGAACAGGATTAGATACCCTGGTAGTCCAGG   772
5   CTGACGCTGAGGAGCGAAAGCTGGGGAGCGAACAGGATTAGATACCCTGGTAGTCCAGG   775
6   CTGACGCTGAGGAGCGAAAGCTGGGGAGCGAACAGGATTAGATACCCTGGTAGTCCAGG   778
7   CTGACGCTGAGGAGCGAAAGCTGGGGAGCGAACAGGATTAGATACCCTGGTAGTCCAGG   749
8   CTGACGCTGAGGAGCGAAAGCTGGGGAGCGAACAGGATTAGATACCCTGGTAGTCCAGG   720
9   CTGACGCTGAGGAGCGAAAGCTGGGGAGCGAACAGGATTAGATACCCTGGTAGTCCAGG   776
C   CTGACGCTGAGGAGCGAAAGCTGGGGAGCGAACAGGATTAGATACCCTGGTAGTCCAGG 790       800       810       820       830       840
1   CCGTAAACGGTGGATGCTGGATGTGGGCCCTTCCACGGGTCCGTGTCGGAGCTAACG    826
2   CCGTAAACGGTGGATGCTGGATGTGGGCCCTTCCACGGCTCCGTGTCGGAGCTAACG    823
3   CCGTAAACGGTGGATGCTGGATGTGGGCCCTTCCACGGGTCCGTGTCGGAGCTAACG    837
4   CCGTAAACGGTGGATGCTGGATGTGGGCCCTTCCACGGGTCCGTGTCGGAGCTAACG    832
5   CCGTAAACGGTGGATGCTGGATGTGGGCCCTTCCACGGGTCCGTGTCGGAGCTAACG    835
6   CCGTAAACGGTGGATGCTGGATGTGGGCCCTTCCACGGGTCCGTGTCGGAGCTAACG    838
7   CCGTAAACGGTGGATGCTGGATGTGGGCCCTTCCACGGGTCCGTGTCGGAGCTAACG    809
8   CCGTAAACGGTGGATGCTGGATGTGGCACCCTTCCACGGGTCCGTGTCGGAGCTAACG   779
9   CCGTAAACGGTGGATGCTGGATGTGGGCCCTTCCACGGGTCCGTGTCGGAGCTAACG    836
C   CCGTAAACGGTGGATGCTGGATGTGGGCCCTTCCACGGGTCCGTGTCGGAGCTAACG 850       860       870       880       890       900
1   CGTTAAGCATCCCGCCTGGGGAGTACGGCCGCAAGGCTAAAACTCAAAGAAATTGACGGG  886
2   CGTTAAGCATCCCGCCTGGGGAGTACGGCCGCAAGGCTAAAACTCAAAGAAATTGACGGG  883
3   CGTTAAGCATCCCGCCTGGGGAGTACGGCCGCAAGGCTAAAACTCAAAGAAATTGACGGG  897
4   CGTTAAGCATCCCGCCTGGGGAGTATGGCCGCAAGGCTAAAACTCAAAGAAATTGACGGG  892
5   CGTTAAGCATCCCGCCTGGGGAGTACGGCCGCAAGGCTAAAACTCAAAGAAATTGACGGG  895
6   CGTTAAGCATCCCGCCTGGGGAGTACGGCCGCAAGGCTAAAACTCAAAGAAATTGACGGG  898
7   CGTTAAGCATCCCGCCTGGGGAGTACGGCCGCAAGGCTAAAACTCAAAGAAATTGACGGG  869
8   CGTTAAGCATCCCGCCTGGGGAGTACGGCCGCAAGGCTAAAACTCAAAGAAATTGACGGG  839
9   CGTTAAGCATCCCGCCTGGGGAGTACGGCCGCAAGGCTAAAACTCAAAGAAATTGACGGG  896
C   CGTTAAGCATCCCGCCTGGGGAGTACGGCCGCAAGGCTAAAACTCAAAGAAATTGACGGG 910       920       930       940       950       960
1   GGCCCGCACAAGCGGCGGAGCATGCGGATTAATTCGATGCAACGCGAAGAACCTTACCT   946
2   GGCCCGCACAAGCGGCGGAGCATGCGGATTAATTCGATGCAACGCGAAGAACCTTACCT   943
3   GGCCCGCACAAGCGGCGGAGCATGCGGATTAATTCGATGCAACGCGAAGAACCTTACCT   957
4   GGCCCGCACAAGCGGCGGAGCATNCGGATTAATTCGATGCAACGCGAAGAACCTTACCT   952
5   GGCCCGCACAAGCGGCGGAGCATGCGGATTAATTCGATGCAACGCGAAGAACCTTACCT   955
6   GGCCCGCACAAGCGGCGGAGCATGCGGATTAATTCGATGCAACGCGAAGAACCTTACCT   958
7   GGCCCGCACAAGCGGCGGAGCATGCGGATTAATTCGATGCAACGCGAAGAACCTTACCT   929
8   GGCCCGCACAAGCGGCGGAGCATGCGGATTAATTCGATGCAACGCGAAGAACCTTACCT   899
9   GGCCCGCACAAGCGGCGGAGCATGCGGATTAATTCGATGCAACGCGAAGAACCTTACCT   956
C   GGCCCGCACAAGCGGCGGAGCAT-CGGATTAATTCGATGCAACGCGAAGAACCTTACCT
```

Figure 2A continued...

```
          970       980       990      1000      1010      1020
1  GGCTTGACATGT  C GAC       GAGA          TCCCTTCGGGGC G TTCACAGG 1006
2  GGCTTGACATGT    GACA       AGAGATG   C TCCCTTCGGGGC G TTCACAGG 1003
3  GGTTGACATGT  CC GAC A    CAGAGAT    G TTCCCTTCGGGGC G TTCACAGG 1017
4  GGCTTGACATGT  CC GAC A    A AGAGAT       TCCCTTCGGGGC G TTCACAGG 1012
5  GGCTTGACATGT     GACA        AGAGAT        TCCCTTCGGGGC G TTCACAGG 1015
6  GGCTTGACATGT  CC GAC A    C AGAGAT        TCCCTTCGGGGC G TTCACAGG 1019
7  GGCTTGACATGT  CC GAC  T C  AGAGAT        CTCCCTTCGGGGC G TTCACAGG  989
8  GGCTTGACATGT  CC GACA       AGAGAT         TCCCTTCGGGGC G ATTCACAGG  959
9  GGCTTGACATGT  CC GAC        GAGAC         TCCCTTCGGGGC G TTCACAGG 1016
C  GGCTTGACATGT     GAC        GAGA          TCCCTTCGGGGC G TTCACAGG 1030      1040      1050      1060      1070      1080
1  TGGTGCATGGTCGTCGTCAGCTCGTGTCGTGAGATGTTGGGT AAGTCCCGCAACGAGCG 1066
2  TGGTGCATGGTCGTCGTCAGCTCGTGTCGTGAGATGTTGGGT AAGTCCCGCAACGAGCG 1063
3  TGGTGCATGGTCGTCGTCAGCTCGTGTCGTGAGATGTTGGGT AAGTCCCGCAACGAGCG 1077
4  TGGTGCATGGTCGTCGTCAGCTCGTGTCGTGAGATGTTGGGT AAGTCCCGCAACGAGCG 1072
5  TGGTGCATGGTCGTCGTCAGCTCGTGTCGTGAGATGTTGGGT AAGTCCCGCAACGAGCG 1075
6  TGGTGCATGGTCGTCGTCAGCTCGTGTCGTGAGATGTTGGGT AAGTCCCGCAACGAGCG 1078
7  TGGTGCATGGTCGTCGTCAGCTCGTGTCGTGAGATGTTGGGT AAGTCCCGCAACGAGCG 1049
8  TGGTGCATGGTCGTCGTCAGCTCGTGTCGTGAGATGTTGGGT AAGTCCCGCAACGAGCG 1019
9  TGGTGCATGGTCGTCGTCAGCTCGTGTCGTGAGATGTTGGGTCAAGTCCCGCAACGAGCG 1076
C  TGGTGCATGGTCGTCGTCAGCTCGTGTCGTGAGATGTTGGGT AAGTCCCGCAACGAGCG 1090      1100      1110      1120      1130      1140
1  CAACCCTCGCC T GTGTTGCCAGC   GT ATG   GGGAACTC G  GGGACCGCCGGGGT 1126
2  CAACCCTCGCC T GTGTTGCCAGC   GT ATG   GGGAACTCA   GGGACCGCCGGGGT 1123
3  CAACCCTCGCC   GTGTTGCCAGC   GT ATC   GGGAACTCA   GGGACCGCCGGGGT 1137
4  CAACCCTCGCC  GNGTTGCCAGC   GT ATC   GGGACCGCCGGGGT 1132
5  CAACCCTCGCC T GTGTTGCCAGC   GT AT    G GGGAACTCA   GGGACCGCCGGGGT 1135
6  CAACCCTCGCC T GTGTTGCCAGC   GT ATC   GGGAACTCA   RGGACCGCCGGGGT 1138
7  CAACCCTCGCC T GTGTTGCCAGC   GT ATC   GGGAACTCA C  GGGACCGCCGGGGT 1109
8  CAACCCTCGCC T GTGTTGCCAGC   GT ATG   GGGAACTCA   AGGGACCGCCGGGGT 1079
9  CAACCCTCGCC T GTGTTGCCAGC   GT ATG   GGGAACTCA    GGGACCGCCGGGGT 1136
C  CAACCCTCGCC  G*GTTGCCAGC   GT ATC   GGGAACTC    GGGACCGCCGGGGT 1150      1160      1170      1180      1190      1200
1  TAAC  CGGAGGAAGG GGGGATGACGTCAGATCATCATGCCCCTTACGTC AGGGCTTCA 1186
2  TAAC  CGGAGGAAGG GGGGATGACGTCAGATCATCATGCCCCTTACGTC AGGGCTTCA 1183
3  TAAC  CGGAGGAAGG GGGGATGACGTCAGATCATCATGCCCCTTACGTC AGGGCTTCA 1197
4  TAAC  CGGAGGAAGG GGGGATGACGTCAGATCATCATGCCCCTTACGTC AGGGCTTCA 1192
5  TAAC  CGGAGGAAGG GGGGATGACGTCAGATCATCATGCCCCTTACGTC AGGGCTTCA 1195
6  TAAC  CGGAGGAAGG GGGGATGACGTCAGATCATCATGCCCCTTACGTC AGGGCTTCA 1198
7  TAAC  CGGAGGAAGG GGGGATGACGTCAGATCATCATGCCCCTTACGTC AGGGCTTCA 1169
8  TAA   CGGAGGAAGG GGGGATGACGTCAGATCATCATGCCCCTTACGTC AGGGCTTCA 1139
9  TAAC  CGGAGGAAGG GGGGATGACGTCAGATCATCATGCCCCTTACGTC AGGGCTTCA 1196
C  TAAC  CGGAGGAAGG GGGGATGACGTCAGATCATCATGCCCCTTACGTC AGGGCTTCA
```

Figure 2A continued...

```
           1210       1220       1230       1240       1250       1260
1  CGCATGCTACAATGGCCGGTACAACGGGATGCGACGCGGTGACGCGGAGCGGATCCCTTA 1246
2  CGCATGCTACAATGGCCGGTACAACGAGATGCGACATGGCGACAGGAAGCGGATCCCTTA 1243
3  CGCATGCTACAATGGCCGGTACAACGGGATGCGACATGGCGACATGGAGCGGATCCCTGA 1257
4  CGCATGCTACAATGGCCGGTACAACGGGATGCGACATGGCGACATGGAGCGGATCCCTGA 1252
5  CGCATGCTACAATGGCCGGTACAACGGATGCGACATGGCGACATGGAGCGGATCCCTGA 1255
6  CGCATGCTACAATGGCCGGTACAACGGATGCGACATGGCGACATGGAGCGGATCCCTGA 1258
7  CGCATGCTACAATGGCCGGTACAACGGGATGCGACATGGCGACATGGAGCGGATCCCTTA 1229
8  CGCATGCTACAATGGCCGGTACAACGAGATGCGACATGGCGACATGGAGCGGATCCCTTA 1199
9  CGCATGCTACAATGGCCGGTACAACGGGATGCGACATGGCGACATGGAGCGGATCCCTTA 1256
C  CGCATGCTACAATGGCCGGTACAACGGGATGCGACNGGCGACNNGAGCGGATCCCTNA 1270       1280       1290       1300       1310       1320
1  AAACCGGTCTCAGTTCGGATCGAGCTGCAACTCGACTCGTGAAGGCGGAGTCGCTAG 1306
2  AAACCGGTCTCAGTTCGGATCGAGCTGCAACTCGACTCGTGAAGGCGGAGTCGCTAG 1303
3  AAACCGGTCTCAGTTCGGATCGAGCTGCAACTCGACTCGTGAAGGCGGAGTCGCTAG 1317
4  AAACCGGTCTCAGTTCGGATCGAGCTGCAACTCGACTCGTGAAGGCGGAGTCGCTAG 1312
5  AAACCGGTCTCAGTTCGGATCGAGCTGCAACTCGACTCGTGAAGGCGGAGTCGCTAG 1315
6  AAACCGGTCTCAGTTCGGATCGAGCTGCAACTCGACTCGTGAAGGCGGAGTCGCTAG 1316
7  AAACCGGTCTCAGTTCGGATCGAGCTGCAACTCGACTCGTGAAGGCGGAGTCGCTAG 1289
8  AAACCGGTCTCAGTTCGGATCGAGCTGCAACTCGACTCGTGAAGGCGGAGTCGCTAG 1259
9  AAACCGGTCTCAGTTCGGATCGAGCTGCAACTCGACTCGTGAAGGCGGAGTCGCTAG 1316
C  AAACCGGTCTCAGTTCGGATCGAGCTGCAACNCGNCTNNTGAAGGCGGAGTCGCTAG 1330       1340       1350       1360       1370       1380
1  TAATCGCGGATCAGCAACGCCGCGGTGAATGCGTTCCCGGGCCTTGTACACACCGCCCGT 1366
2  TAATCGCGAATCAGCAACGCCGCGGTGAATGCGTTCCCGGGCCTTGTACACACCGCCCGT 1363
3  TAATCGCGGATCAGCAACGCCGCGGTGAATGCGTTCCCGGGCCTTGTACACACCGCCCGT 1377
4  TAATCGCGGATCAGCAACGCCGCGGTGAATGCGTTCCCGGGCCTTGTACACACCGCCCGT 1372
5  TAATCGCGGATCAGCAACGCCGCGGTGAATGCGTTCCCGGGCCTTGTACACACCGCCCGT 1375
6  TAATCGCGGATCAGCAACGCCGCGGTGAATGCGTTCCCGGGCCTTGTACACACCGCCCGT 1378
7  TAATCGCGGATCAGCAACGCCGCGGTGAATGCGTTCCCGGGCCTTGTACACACCGCCCGT 1349
8  TAATCGCGGATCAGCAACGCCGCGGTGAATGCGTTCCCGGGCCTTGTACACACCGCCCGT 1319
9  TAATCGCGGATCAGCAACGCCGCGGTGAATGCGTTCCCGGGCCTTGTACACACCGCCCGT 1376
C  TAATCGCGNATCAGCAACGNCGCGGTGAATGCGTTCCCGGGCCTTGTACACACCGCCCGT 1390       1400       1410       1420       1430       1440
1  CAAGTCATGAAAGTGGGCAGCACCCGAAGCCGGTGGCCCAACCTTTT---GGGGGGAGCC 1423
2  CAAGTCATGAAAGTGGGCAGCACCCGAAGCCGGTGGCCCAACCTTTT---GGAGGGAGCC 1420
3  CAAGTCATGAAAGTGGGCAGCACCCGAAGCCGGTGGCCTAACCCTTGT--GGGGGGAGCC 1435
4  CAAGTCATGAAAGTGGGCAGCACCCGAAGCCGGTGGCCTAACCTTGT--GGGGGGAGCC 1430
5  CAAGTCATGAAAGTGGGCAGCACCCGAAGCCGGTGGCCTAACCTTGT--GGGGGGAGCC 1433
6  CAAGTCATGAAAGTGGGCAGCACCCGAAGCCGGTGGCCTAACCTTCTTGGGGGGGAGCC 1438
7  CAAGTCATGAAAGTGGGCAGCACCCGAAGCCGGTGGCCTAACTCGCAA-GAGGGGGAGCC 1408
8  CAAGTCATGAAAGTGGGCAGCACCCGAAGCCGGTGGCCTAACCTTTTG-GAGGG--AGCC 1376
9  CAAGTCATGAAAGTGGGCAGCACCCGAAGCCGGTGGCCCAACCGCGA-GGGGGGGAGCC 1435
C  CAAGTCATGAAAGTGGGCAGCACCCGAAGCCGGTGGCCNAACN+++::+GNGNNAGCC
```

Figure 2A continued…

```
       1450       1460       1470       1480       1490       1500
1  GTCTAAGGTGAGATTCGTGATTGGGACTAA--------------------------------  1453
2  GTCTAAGG------------------------------------------------------  1428
3  GTCTAAGGTGAGGCTCGTGATTGGGACTAAGTCGTAACAAGGTAGCCGTACCGGAAGGTG    1495
4  GTCTAAGGTGAGGCTCGTGATTGGGACTAAGTCGTAACAAGGTAGCCGTACCGGAAGGTG    1490
5  GTCTAAGGTGAGGCTCGTGATTGGGACTAAGTCGTAACAAGGTAGCCGTACCGGAAGGTG    1493
6  GNCTAAGGTGAGGNTCGTGATTGGGACTAAGTCGTAACAAGGTAGCCGTACCGGAAGGTG    1493
7  GTCTAAGG------------------------------------------------------  1416
8  GTCTAAGG------------------------------------------------------  1384
9  GTCTAAGGTGAGGTCCGCGATTGGGACTAAGTCGTAACAAGGTAGCCGTACCGGAAGGTG    1495
C  G*CTAAGG++++::;++:++++++++++++:::::::::::::::::::::::::::::::

1510
1  ------------------                                              1453
2  ------------------                                              1428
3  CGGCTGGATCACCTCCTTA                                             1514
4  CGGCTGGATCACCTCCTTA                                             1509
5  CGGCTGGATCACCTCCTTA                                             1512
6  CGGTTGGATCACCTCCTTA                                             1517
7  ------------------                                              1416
8  ------------------                                              1384
9  CGGCTGGATCACCTCCTTA                                             1514
C  :::::::::::::::::::
```

Figure 2A continued

Figure 3

TGCATGAGGGTCTGAAGAACGTCGTGGCCGGATCCAACCCGATCGCACTGC
GTCGCGGTGTCGAGAAGGCGTCCGACGCCATCGTCAAGGAGC**TCGTCGCC
TCGGCCAAGGACGTGGAAACCAAGGAGCAGATCG**CGGCTACGGCCACGA
TTTCCGCCGCTGATCCCGAGGTCGGCGACAAGATCGCCGAAGCACTCGACA
AGGTCGGCCAG

Figure 4...

Figure 4 continued...

| | | | | |
|---|---|---|---|---|
| Bifidobacterium pseudocatenulatum | CCGCCGCCGA | TCCGGAAGTC | GGCGAGAAGA | TCGCCGAAGC | TCTTGACAAG 246 |
| Bifidobacterium catenulatum | CCGCAGCCGA | TCCGGAAGTC | GGCGAGAAGA | TCGCTGAGGC | GCTGGACAAG 246 |
| Bifidobacterium dentium | CCGCCGCCGA | TCCGGAAGTC | GGCGAGAAGA | TCGCCGAAGC | GCTGGACAAG 247 |
| Bifidobacterium merycicum | CCGCCGCCGA | TCCTGAAGTT | GGTGAGAAGA | TCGCCGAAGC | CCTGGACAAG 246 |
| Bifidobacterium angulatum DSM 20098 | CCGCCGCCGA | TCCCGAGGTT | GGCGAGAAGA | TCGCCGAAGC | CCTGGACAAG 247 |
| Bifidobacterium pullorum | CCGCCGCCGA | TCCGGAAGTC | GGCGAGAAGA | TCGCCGAGGC | CCTGGACAAG 246 |
| Bifidobacterium gallinarum | CCGCCGCCGA | TCCGGAAGTC | GGCGAGAAGA | TCGCCGAAGC | TCTCGACAAG 246 |
| Bifidobacterium bifidum | CCGCAGCCGA | CCCGAGGTT  | GGCGAGAAGA | TCGCCGAGGC | TCTGGACAAG 246 |
| Bifidobacterium ruminantium | CCGCCGCTGA | TCCGGAAGTC | GGCGAGAAGA | TCGCCGAAGC | TCTCGACAAG 246 |
| Bifidobacterium longum bv. Infantis | CCGCCGCTGA | CCCTGAAGTC | GGCGAGAAGA | TCGCTGAGGC | TCTGGACAAG 246 |
| Bifidobacterium longum | CCGCCGCTGA | CCCTGAGGTC | GGCGAGAAGA | TCGCTGAGGC | TCTGGACAAG 278 |
| Bifidobacterium longum bv. Suis | CCGCCGCTGA | CCCTGAAGTC | GGCGAGAAGA | TCGCTGAGGC | TCTGGACAAG 247 |
| Bifidobacterium breve DSM 20213 | CCGCTGCTGA | CCCCGAGGTC | GGCGAGAAGA | TCGCTGAGGC | TCTGGACAAG 249 |
| Bifidobacterium pseudolongum subsp. globosum | CCGCAGCCGA | TCCCGAGGTC | GGCGAGAAGA | TCGCCGAGGC | GCTCGACAAG 247 |
| Bifidobacterium cuniculi | CCGCCGCCGA | CCCGGAGGTC | GGCGAGAAGA | TCGCCGAAGC | GCTCGACAAG 246 |
| Bifidobacterium choerinum | CGGCCGCCGA | TCCGGAGGTC | GGCGAGAAGA | TCGCCGAGGC | ACTCGACAAG 247 |
| Bifidobacterium thermacidophilum | CTGCTGCTGA | TCCTGAAGTC | GGCGAGAAGA | TCGCCGAGGC | GCTTGACAAG 246 |
| Bifidobacterium boum | CCGCTGCCGA | TCCTGAAGTC | GGCGAGAAGA | TCGCCGAGGC | ACTCGACAAG 246 |
| Bifidobacterium thermophilum | CCGCTGCTGA | CCCTGAGGTC | GGCGAGAAGA | TCGCTGAAGC | GCTCGACAAG 247 |
| Bifidobacterium magnum | CAGCTGCCGA | TCCGGAAGTC | GGCGAGAAGA | TCGCCGAAGC | GCTCGACAAG 246 |
| Bifidobacterium gallicum | CGGCTGCTGA | CCCCGAGGTT | GGCGAGAAGA | TTGCCGAAGC | GCTCGACAAG 248 |
| Bifidobacterium indicum | CCGCCGGAGA | TCCCGAGATC | GGCGCCGAAA | TCGCCGAGGC | CCTGGACAAG 247 |
| Bifidobacterium asteroides | CTGCAGGCGA | CCCCGAGATC | GGCAATGAGA | TCGCCGAAGC | TCTCGACAAG 247 |
| Bifidobacterium coryneforme | CCGCCGGCGA | CCCCGAGATT | GGTGCTGAGA | TTGCCGAGGC | CCTCGACAAG 247 |
| Bifidobacterium psychraerophilum | CAGCCGCTGA | CCCAGAGGTC | GGCGAGAAGA | TCGCGGAAGC | TCTCGACAAG 231 |
| Bifidobacterium minimum | CCGCTGCCGA | CCCCGAGGTC | GGAGAGAAGA | TCGCCGAGGC | TCTGGACAAG 246 |
| Bifidobacterium tsurumiense | CCGCTGCGGA | TCCTGAGGTT | GGCGAGAAGA | TCGCCGAAGC | CTTGGATAAG 249 |
| Bifidobacterium animalis | CCGCAGGTGA | CCCCGAGGTG | GGCGAGAAGA | TCGCCGAGGC | TCTCGACAAG 203 |
| Bifidobacterium adolescentis | CCGCCGCTGA | TCCCGAGGTC | GGCGAGAAGA | TCGCCGAGGC | TCTGGACAAG 203 |
| Bifidobacterium crudilactis | CCGCCGCCGA | TCCCGAGGTT | GGCGAGAAGA | TCGCCGAAGC | TCTGGACAAG 184 |
| Bifidobacterium vercorsense | CCGCCGCTGA | TCCCGAGGTC | GGCGACAAGA | TCGCCGAAGC | ACTCGACAAG 203 |
| Consensus | C.GC.G..GA | .CC.GA..T. | GG.....A.A | T.GC.GA.GC | ...T.GA.AAG |

| | | | | |
|---|---|---|---|---|
| Bifidobacterium pseudocatenulatum | GTTGGCCAGG | ACGGCGTCGT | GACCGTTGAG | GACAACAACC | GCTTCGGCCT 296 |
| Bifidobacterium catenulatum | GTTGGCCAGG | ATGGTGTTGT | GACCGTTGAG | GACAACAACC | GTTTCGGTTT 296 |
| Bifidobacterium dentium | GTCGGCCAGG | ATGGCGTCGT | GACCGTCGAG | GACAACAACC | GCTTCGGCCT 297 |
| Bifidobacterium merycicum | GTCGGCCAGG | ATGGCGTCGT | GACCGTTGAA | GACAACAACC | GCTTCGGCCT 296 |
| Bifidobacterium angulatum DSM 20098 | GTTGGCCAGG | ACGGCGTCGT | GACCGTTGAG | GACAACAACC | GCTTCGGCCT 297 |
| Bifidobacterium pullorum | GTCGGCCAGG | ACGGCGTCGT | GACCGTTGAG | GACAACAACC | GCTTCGGCCT 296 |
| Bifidobacterium gallinarum | GTCGGCCAGG | ACGGCGTCGT | GACCGTTGAG | GACAACAACC | GCTTCGGCCT 296 |
| Bifidobacterium bifidum | GTCGGTCAGG | ACGGCGTCGT | GACCGTCGAG | GACAACAACC | GCTTCGGCCT 296 |
| Bifidobacterium ruminantium | GTCGGCCAGG | ACGGTGTCGT | GACCGTCGAG | GACAACAACC | GCTTCGGACT 296 |
| Bifidobacterium longum bv. Infantis | GTCGGCCAGG | ACGGCGTTGT | GACCGTTGAA | GACAACAACC | GCTTCGGCCT 296 |
| Bifidobacterium longum | GTCGGCCAGG | ACGGCGTTGT | GACCGTTGAA | GACAACAACC | GCTTCGGCCT 278 |
| Bifidobacterium longum bv. Suis | GTCGGCCAGG | ACGGCGTCGT | GACCGTTGAA | GACAACAACC | GCTTCGGCCT 297 |
| Bifidobacterium breve DSM 20213 | GTCGGCCAGG | ATGGCGTTGT | GACCGTTGAA | GATAACAACC | GCTTCGGTCT 290 |
| Bifidobacterium pseudolongum subsp. globosum | GTCGGCCAGG | ATGGTGTGGT | GACCGTCGAG | GACAACAACC | GCTTCGGTCT 297 |
| Bifidobacterium cuniculi | GTCGGCCAGG | ACGGCGTCGT | GACCGTCGAG | GACAACAACC | GCTTCGGCCT 296 |
| Bifidobacterium choerinum | GTCGGCCAGG | ACGGTGTCGT | GACCGTCGAG | GACAACAACC | GCTTCGGCCT 297 |
| Bifidobacterium thermacidophilum | GTCGGCCAGG | ATGGCGTCGT | GACCGTCGAG | GACAACAACC | GCTTCGGCCT 296 |
| Bifidobacterium boum | GTCGGCCAGG | ATGGCGTCGT | GACTGTCGAG | GACAACAACC | GCTTCGGTCT 296 |
| Bifidobacterium thermophilum | GTCGGCCAGG | ATGGTGTGGT | GACCGTCGAG | GACAACAACC | GCTTCGGTCT 297 |
| Bifidobacterium magnum | GTCGGCCAGG | ATGGCGTCGT | GACCGTGGAA | GACAACAATC | GTTTCGGCTT 296 |
| Bifidobacterium gallicum | GTCGGCCAGG | ATGGCGTCGT | GACCGTGGAA | GACAACAATC | GTTTCGGCTT 298 |
| Bifidobacterium indicum | GTCGGCCAGG | ATGGCGTCGT | CACCGTCGAG | GACAACAACC | GCTTCGGCCT 297 |
| Bifidobacterium asteroides | GTCGGCCAGG | ACGGCGTGGT | CACCGTCGAG | GACAACAACC | GCTTCGGACT 297 |
| Bifidobacterium coryneforme | GTGGGCCAGG | ATGGTGTGGT | CACCGTCGAG | GACAACAACC | GCTTCGGTCT 297 |
| Bifidobacterium psychraerophilum | GTCGGCCAGG | ACGGCGTTGT | AACCGTCGAG | GACAACAACC | GCTTCGGTCT 281 |
| Bifidobacterium minimum | GTCGGCCAGG | ATGGCGTCGT | CACCGTCGAG | GACAACAACC | GTTTCGGTCT 296 |
| Bifidobacterium tsurumiense | GTCGGACAGG | ACGGTGTGGT | CACCGTTGAA | GACAACAACA | AGTTCGGTTT 299 |
| Bifidobacterium animalis | GTCGGACAG- | ---------- | ---------- | ---------- | ---------- 212 |
| Bifidobacterium adolescentis | GTCGGCCAG- | ---------- | ---------- | ---------- | ---------- 212 |
| Bifidobacterium crudilactis | GTCGGCCAGG | ACGGT----- | ---------- | ---------- | ---------- 199 |
| Bifidobacterium vercorsense | GTCGGCCAG- | ---------- | ---------- | ---------- | ---------- 212 |
| Consensus | GT.GG.CAGG | A.GG.GT.GT | .AC.GT.GA. | GA.AACAA.. | ...TTCGG..T |

Figure 4 continued

Figure 6:
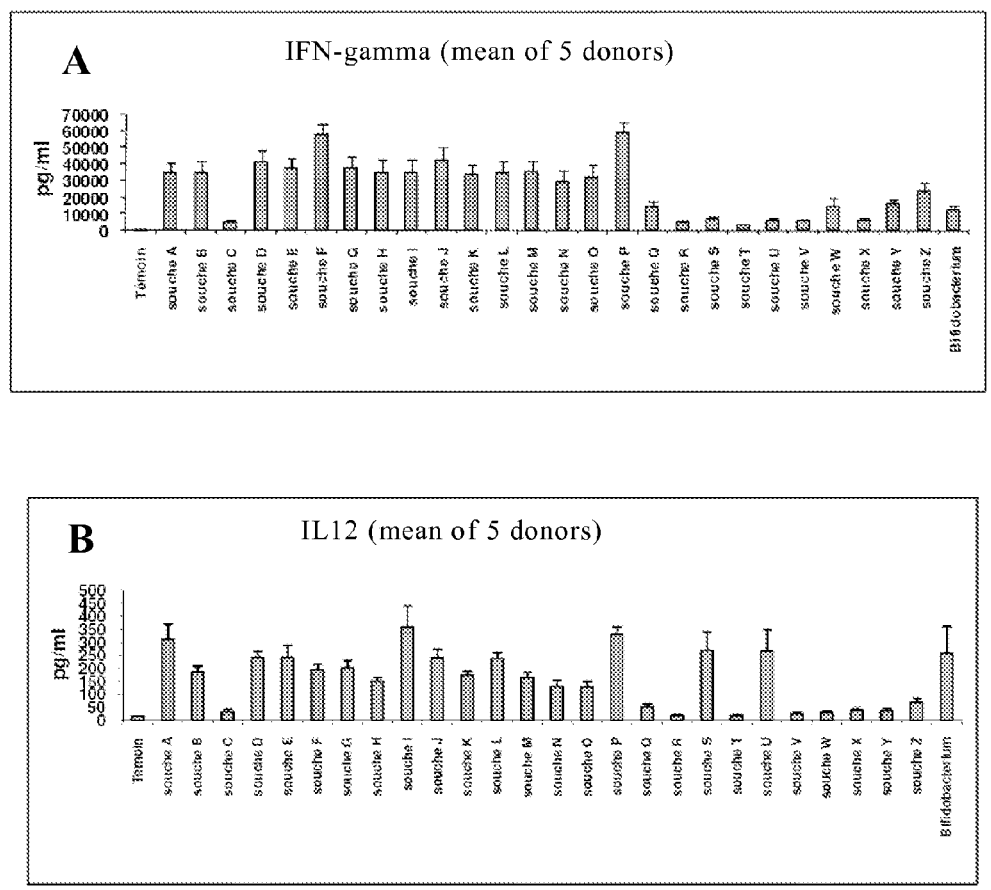

Figure 6 continued
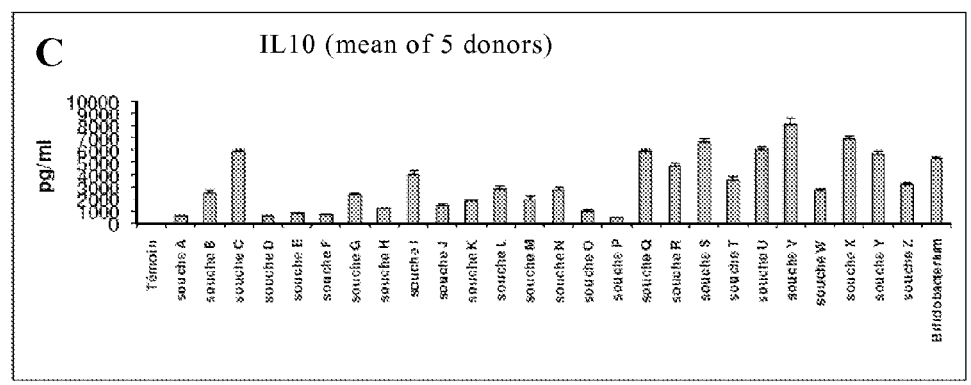
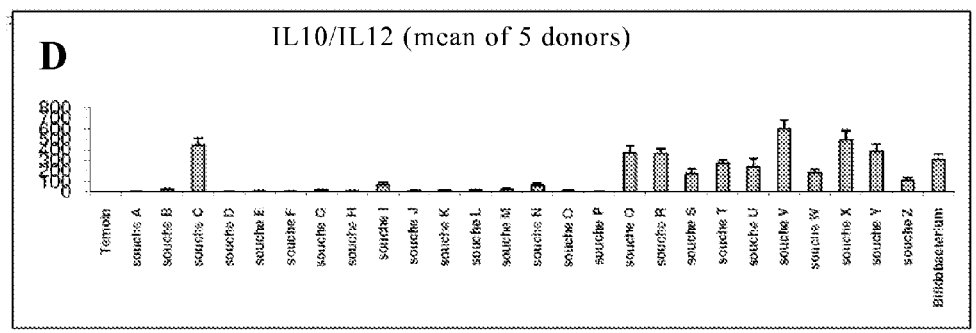

BIFIDOBACTERIAL SPECIES

This is a national stage of PCT/EP08/058,490 filed Jul. 2, 2008, which has a priority of EP 07118938.5 filed Oct. 20, 2007. Both of which are incorporated by reference herein.

The invention relates to a bacterium belonging to the genus *Bifidobacterium*, to probiotic compositions comprising said bacterium, particularly food products, and to the use of said bacterium in the treatment of diseases, such as gastrointestinal diseases.

Bifidobacteria (or bacteria belonging to the *Bifidobacterium* genus) constitute one of the most important populations of human and animal faecal flora. It is generally considered an indication of good health when these bacteria are present at a high rate in faecal flora. For this reason, they are known as probiotic bacteria (beneficial microorganisms which improve the natural balance of intestinal flora when ingested alive). Examples of known Bifidobacteria include *B. adolescentis, B. animalis, B. bifidum, B. breve, B. catenulatum* and *B. longum*, which have been shown to have beneficial technological, organoleptic and probiotic effects.

Bifidobacteria are most commonly found as an additive in fermented milks (yoghurts with "active Bifidus") and thus constitute an economically important commodity. The strains chosen by the milk industry must meet numerous strict requirements, such as resistance to the process of manufacture and survival within the foodstuff. The most commonly used species in France are *B. animalis* subsp. *lactis* and *B. animalis* subsp. *animalis*, which is a subspecies from animal origin, never isolated from humans. In view of the importance of bifidobacteria, there is a great need to identify novel species within this genus having properties optimally matched to the requirements of the food industry. For example, in 2004, a group identified and isolated *Bifidobacterium psychraerophilum* from a porcine caecum (Simpson, P J. et al. (2004) *Int J Syst Evol Microbiol* 54: 401-6). Previously known *Bifidobacterium* had only been able to grow at temperatures between 20° C. and 46-49.5° C. (Biavati, B. et al., (2000), *Annals of Microbiology* 50: 117-131; Dong et al., (2000) *Int J Syst Evol Microbiol* 50 Pt 1:119-25), however, *Bifidobacterium psychraerophilum* demonstrated an advantage over all previous species by growing at between 4 and 10° C. This is beneficial for probiotic compositions as the bacteria are more likely to survive the low storage temperatures of such products and would therefore prolong product shelf-life. There is thus a great need for the identification of further bifidobacterial species, which not only possess unique advantages but also retain the benefits of previously identified bifidobacterial species.

According to a first aspect of the invention there is provided *Bifidobacterium* GC61 or a homolog, descendant or mutant thereof.

GC61 represents a new species of *Bifidobacterium*. The terms GC61, GC61 group, *Bifidobacterium* GC61 and *Bifidobacterium vercorsense* are used interchangeably to refer to this new species of *Bifidobacterium*.

Examples of strains of GC61 discussed herein include FR41/2, FR49/f/2, FR101/h/8, MarV3/22, FR39/1, MarV4/2, MarV1/5, FR66/e/1, MarC1/13, MarF/3, PicD/1, FR70/g/2 and FR47/2. The 16S rRNA genes of FR41/2, FR49/f/2 and FR101/h/8 strains have been sequenced and are designated as Sequence ID No. 1 for the 16S rRNA gene of FR101/h/8; Sequence ID No. 2 for the 16S rRNA gene of FR41/2; and Sequence ID No. 3 for the 16S rRNA gene of FR49/f/2.

Preferably the *Bifidobacterium* GC61 or homolog thereof is a strain selected from any one or more of FR41/2, FR49/f/2, FR101/h/8, MarV3/22, FR39/1, MarV4/2, MarV1/5, FR66/e/1, MarC1/13, MarF/3, PicD/1, FR70/g/2 and FR47/2.

A deposit of *Bifidobacterium* GC61 strain FR41/2 was made to the Collection Nationale de Cultures de Microorganismes (CNCM) at the Institut Pasteur in Paris, the recognized IDA under the Budapest Treaty on the International Recognition of the Deposit of Microorganisms for the Purposes of Patent Procedure on the 9 Jan. 2007, this deposit was accorded accession number CNCMI-3712.

A deposit of *Bifidobacterium* GC61 strain FR49/f/2 was made to the Collection Nationale de Cultures de Microorganismes (CNCM) at the Institut Pasteur in Paris, the recognized IDA under the Budapest Treaty on the International Recognition of the Deposit of Microorganisms for the Purposes of Patent Procedure on the 9 Jan. 2007, this deposit was accorded accession number CNCMI-3713.

Deposits of *Bifidobacterium* GC61 strains FR101/h/8, FR66/e/1, MarF/3, FR70/g/2 and FR47/2 were made to the Belgian Coordinated Collections of Microorganisms (BCCM) Prime Minister's Services, Federal Office for Scientific, Technical and Cultural Affairs (OSTC), the recognized IDA under the Budapest Treaty on the International Recognition of the Deposit of Microorganisms for the Purposes of Patent Procedure on Feb. 16, 2012, and these deposits were accorded accession numbers LMG P-26938, LMG P-26939, LMG P-26937, LMG P-26935, or LMG P26936, respectively.

It will be appreciated that a homolog of *Bifidobacterium* GC61 will be understood to refer to any bifidobacteria strain having DNA sequence homology of greater than about 60% with *Bifidobacterium* GC61 (hereinafter also referred to as GC61). Preferably the sequence homology referred to is across the entire bacterial genome. Preferably, a GC61 homolog is one having greater than about 70% DNA sequence homology with GC61, more preferably the homology is greater than 80%, preferably greater than 90%, more preferably greater than about 95%, especially preferably greater than about 98% or about 99%, or any range between any of the above values. Preferably the degree of DNA homology is determined by DNA-DNA reassociation experiments which determine the degree of homology across the entire genome of two or more bacteria. A method which may be used to determine DNA homology is described in the examples, however the skilled man will appreciate that any other suitable method may also be used.

In addition, or alternatively, a homolog to GC61 may be defined by reference to the degree of sequence homology between specific genes. For example, a bacterium wherein the 16S rDNA sequence is more than 95.45%, preferably more than 97%, more preferably more than 99%, homologous to the 16S rDNA of GC61 may be described as a GC61 homolog. The 16S rDNA sequence of GC61 may be the 16S rDNA consensus sequence referred to in FIG. 1A (Sequence ID No: 4) or it may have the sequence of the 16S rDNA from any GC61 strain. Similarly, or alternatively, a bacterium which has an hsp60 gene with more than 87%, preferably more than 90%, sequence homology to the sequence of the hsp60 gene, or to a consensus sequence from the hsp60 gene, in GC61 may be described as a GC61 homolog. Preferably the consensus sequence of the hsp60 gene is the sequence identified in FIG. 3. Preferably the 16S rDNA sequence or the hsp60 sequence of the FR41/2 or the FR49/f/2 strain of GC61 is used when determining the degree of sequence homology.

Homologs of GC61 may be naturally occurring or may be artificially produced, for example by genetic manipulation.

GC61 was isolated from raw milk during the process for making the cheese "L'etoile du Vercors" which is made by a traditional and manual process. GC61 is present throughout the cheese production process (i.e. from raw milk to the end of maturing), with a statistically significant increase during the process. These bacteria belong to a natural microbial population which takes part in the development of organoleptic properties of the product.

GC61 has an advantage of being isolated from a food production process whereas many previously isolated bifidobacteria species have been extracted from the digestive tracts of humans or animals, thus GC61 is easier to integrate into the manufacturing process and is also easier to stabilise in food and fermented products than many other bifidobacteria species.

GC61 has also been found to be psychotrophic and to be able to grow at temperatures as low as about 12° C. The key advantage of growth at low temperatures is that GC61 bacteria are more likely to survive low storage temperatures than most other probiotic bacterial compositions, which would therefore prolong their shelf-life.

Further advantages of GC61 bacteria are that they provide a good resistance to stomach acidity, the biliary salts and to the intestinal enzymes (pepsin).

A still further advantage of GC61 bacteria is that they are air/oxygen resistant, that is, they are aerotolerant.

A yet further advantage of GC61 bacteria, and the strain FR49/f/2 in particular, is that it has a surprising immunomodulatory effect, and may cause a high level of production of the cytokine IL10, but a low level of IL12. This ratio of IL10 to IL12 is indicative of anti-inflammatory properties. Anti-inflammatory properties were also demonstrated in vivo on an experimental model of colitis in mice.

The *Bifidobacterium* GC61 may be in the form of viable cells.

In addition, or as an alternative, to viable cells, killed cultures of *Bifidobacterium* GC61 containing beneficial factors expressed by the *Bifidobacterium* GC61 cells may be useful.

The *Bifidobacterium* GC61 may be in the form of a biologically pure culture.

Mutants of *Bifidobacterium* GC61 include strains with conservative or degenerative changes in the genetic code. Mutants may be naturally occurring or genetically engineered.

According to a second aspect of the invention there is provided a composition comprising *Bifidobacterium* GC61 as hereinbefore defined and one or more acceptable excipients. Preferably the composition is a probiotic composition.

It will be appreciated that an acceptable excipient will be well known to the person skilled in the art of probiotic composition preparation.

Examples of acceptable excipients include: sugars such as sucrose, isomerised sugar, glucose, fructose, palatinose, trehalose, lactose and xylose; sugar alcohols such as sorbitol, xylitol, erythritol, lactitol, palatinol, reduced glutinous starch syrup and reduced glutinous maltose syrup; emulsifiers such as sucrose esters of fatty acids, glycerin esters of fatty acids and lecithin; thickeners (stabilizers) such as carrageenan, xanthan gum, guar gum, pectin and locust bean gum; acidifiers such as citric acid, lactic acid and malic acid; fruit juices such as lemon juice, orange juice and berry juice; vitamins such as vitamin A, vitamin B, vitamin C, vitamin D and vitamin E; and minerals such as calcium, iron, manganese and zinc.

Compositions of the invention may be prepared by admixture, suitably at ambient temperature and atmospheric pressure, usually adapted for oral administration. Such compositions may be in the form of tablets, capsules, oral liquid preparations, conventional food products, powders, granules, lozenges, reconstitutable powders or suspensions.

Tablets and capsules for oral administration may be in unit dose form, and may contain one or more conventional excipients, such as binding agents, fillers, tabletting lubricants, disintegrants, and acceptable wetting agents. The tablets may be coated according to methods well known in pharmaceutical practice.

Oral liquid preparations may be in the form of, for example, aqueous or oily suspensions, solutions, emulsions, syrups or elixirs, or may be in the form of a dry product for reconstitution with water or another suitable vehicle before use. Such liquid preparations may contain conventional additives such as suspending agents, emulsifying agents, non-aqueous vehicles (which may include edible oils), preservatives, and if desired, conventional flavourings or colourants.

In one preferred embodiment, the composition of the invention is formulated as a conventional food product, more preferably, a dairy based product (e.g. fermented milk, vegetable milk, soybean milk, butter, cheese or yoghurt) or fruit juice. The composition is preferably formulated as a food or drink for adult and/or infant humans and/or animals. In an alternative embodiment, the composition is formulated as a lyophilised or spray-dried powder. As well as exhibiting a probiotic effect (i.e. maintaining the balance of intestinal flora), bifidobacteria are also generally believed to be of potential use in the treatment and/or prophylaxis of a variety of disorders, such as gastrointestinal diseases, Crohn's disease, colitis, ulcerative colitis, inflammatory disorders, immunodeficiency, inflammatory bowel disease, irritable bowel syndrome, cancer (particularly of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplant rejection, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis; acne vulgaris and/or cholesterol excesses.

GC61 may be present in the composition at more than about $10^6$ cfu per gram.

According to a further aspect of the invention there is provided *Bifidobacterium* GC61 for use as a therapeutic or prophylactic substance, in particular in the treatment and/or prophylaxis of any one or more of the aforementioned disorders.

The invention further provides a use of *Bifidobacterium* GC61 in the preparation of a medicament for the treatment and/or prophylaxis of any one or more of the aforementioned disorders.

According to a further aspect, the invention provides *Bifidobacterium* GC61 for use in the treatment and/or prophylaxis of any one or more of the aforementioned disorders.

According to a yet further aspect the invention provides a method of treatment and/or prophylaxis of any one or more of the aforementioned disorders, in a human or animal subject, which comprises administering to the subject a therapeutically effective amount of *Bifidobacterium* GC61.

Bifidobacterium GC61 may be used in combination with other therapeutic agents, for example, other medicaments known to be useful in the treatment and/or prophylaxis of gastrointestinal diseases (e.g. diarrhoea), cancer, cholesterol excesses, allergies, infection or any one or more of the aforementioned disorders.

Thus, as a further aspect of the invention, there is provided a composition comprising a combination of Bifidobacterium GC61 together with a further therapeutic agent or agents.

The combinations referred to above may conveniently be presented for use in the form of a probiotic composition and thus probiotic compositions comprising a combination as defined above together with one or more excipients provides a further aspect of the invention. The individual components of such combinations may be administered either sequentially or simultaneously in separate or combined probiotic compositions.

In a preferred embodiment, Bifidobacterium GC61 is combined and/or used with other bifidobacteria or other probiotic bacteria such as: bacteria belonging to the genus Lactobacillus such as Lactobacillus acidophilus, Lactobacillus gasseri, Lactobacillus plantarum, Lactobacillus buchneri, Lactobacillus casei, Lactobacillus johnsonii, Lactobacillus gallinarum, Lactobacillus amylovorus, Lactobacillus brevis, Lactobacillus rhamnosus, Lactobacillus kefir, Lactobacillus paracasei, Lactobacillus crispatus, Lactobacillus delbrueckii subsp. delbrueckii, Lactobacillus delbrueckii subsp. bulgaricus, Lactobacillus helveticus, Lactobacillus zeae and Lactobacillus salivalius; bacteria belonging to the genus Streptococcus such as Streptococcus thermophilus; bacteria belonging to genus Lactococcus such as Lactococcus lactis subsp. cremoris and Lactococcus lactis subsp. lactis; bacteria belonging to the genus Bacillus such as Bacillus subtilis; bacteria belonging to the Bifidobacterium genus such as Bifidobacterium crudilactis; and/or yeast belonging to the genus Saccharomyces, Torulaspora and/or Candida such as Saccharomyces cerevisiae, Torulaspora delbrueckii and Candida kefyr.

According to another aspect of the invention, there is provided Bifidobacterium GC61 or a homolog, descendent or mutant thereof, for use as an immunomodulatory and/or anti-inflammatory probiotic. Preferably the use is to induce IL-10 production in a mammalian subject. Preferably IL-10 is produced by PBMC's.

According to a further aspect of the invention, there is provided the use of Bifidobacterium GC61 or a homolog, descendent or mutant thereof, in the preparation of a medicament for the treatment of inflammation in a mammalian subject. Preferably the inflammation is of the gastro-intestinal tract. Preferably the medicament is for the treatment of colitis.

According to a yet further aspect of the invention, there is provided Bifidobacterium GC61 or a homolog, descendent or mutant thereof, for use in the treatment of inflammation in a mammalian subject. Preferably the inflammation is of the gastro-intestinal tract. Preferably the Bifidobacterium GC61 or a homolog, descendent or mutant thereof is for use in the treatment of colitis.

According to another aspect of the invention, there is provided a method of treating inflammation in a mammalian subject comprising administering a therapeutically effective amount of Bifidobacterium GC61 to the mammalian subject. Preferably the inflammation is of the gastro-intestinal tract. Preferably the method is for the treatment of colitis.

Preferably the Bifidobacterium GC61 or a homolog, descendent or mutant thereof, stimulates IL-10 production in a mammalian subject. Preferably Bifidobacterium GC61 or a homolog, descendent or mutant thereof reduces IL-12 production in a mammalian subject. Preferably the Bifidobacterium GC61 or a homolog, descendent or mutant thereof does not stimulate IL-12 production in a mammalian subject.

Preferably the mammalian subject is a human.

The Bifidobacterium GC61 used in any aspect of the invention may be any of the previously mentioned strains. For example, the stain may be the FR41/2 or the FR49/f/2 strain. If the Bifidobacterium GC61 is for use as immunomodulatory and/or an anti-inflammatory probiotic/agent, and/or for use in the treatment of inflammation, the strain may be FR49/f/2.

It is understood that all optional and/or preferred features of one aspect or embodiment of the invention may be applied to all other aspects or embodiments of the invention described herein.

Embodiments of the invention will now be described merely by way of example with reference to the accompanying figures in which:

FIG. 1A—shows an alignment of the 16S rRNA gene sequences obtained from the GC61 strains FR101/h/8 (Sequence ID No: 1), FR41/2 (Sequence ID No: 2) and FR49/f/2 (Sequence ID No: 3) (called respectively 1, 2 and 3). The alignment was performed using ClustalW and Edtaln softwares. The consensus sequence (Sequence ID No: 4) (called C in the alignment) shows 100% of homology between the 3 strains from base number 2 to base number 1452. The consensus is shown by a sequence of characters which, according to the situation encountered in a given position, will include:

"•" if the character has a majority representation>=20%
":" If the character has a majority representation>=40%
"+" If the character has a majority representation>=60%
"*" If the character has a majority representation>=80%
the character itself, if it is the same for all sequences;

FIG. 1B—shows the 1452 bp DNA consensus sequence which encodes the 16S rRNA in Bifidobacterium vercorsense based on the 3 partial sequences from strains FR101/h/8, FR41/2 and FR49/f/2.

Figure 2A:
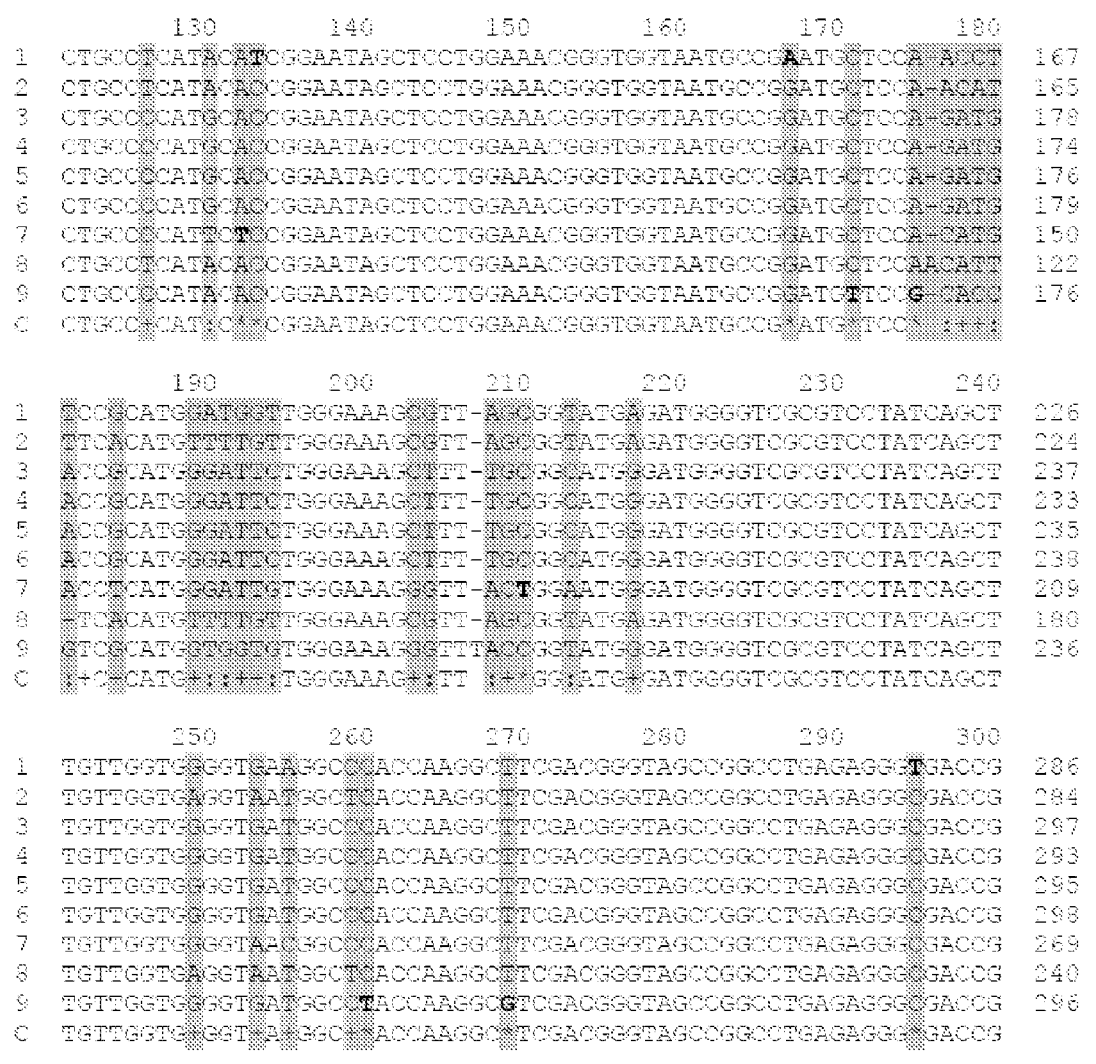
Figure 5:
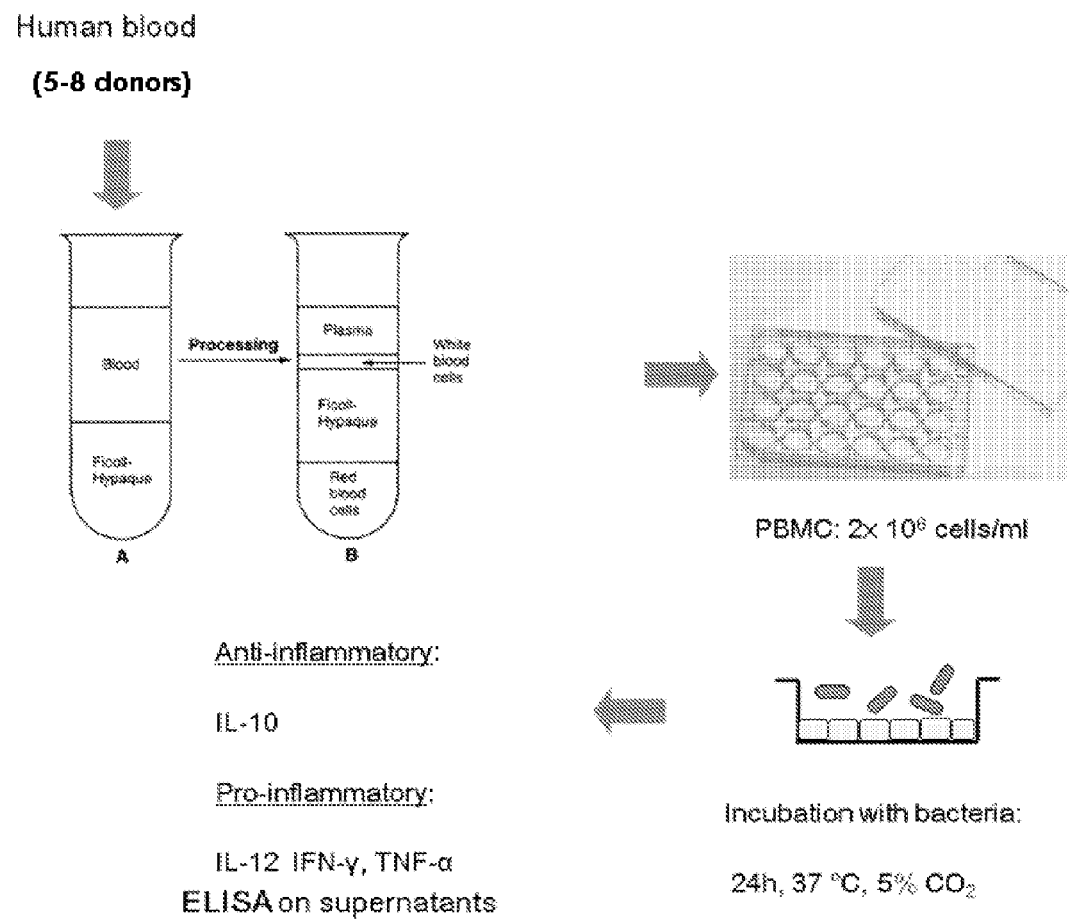
Figure 7:
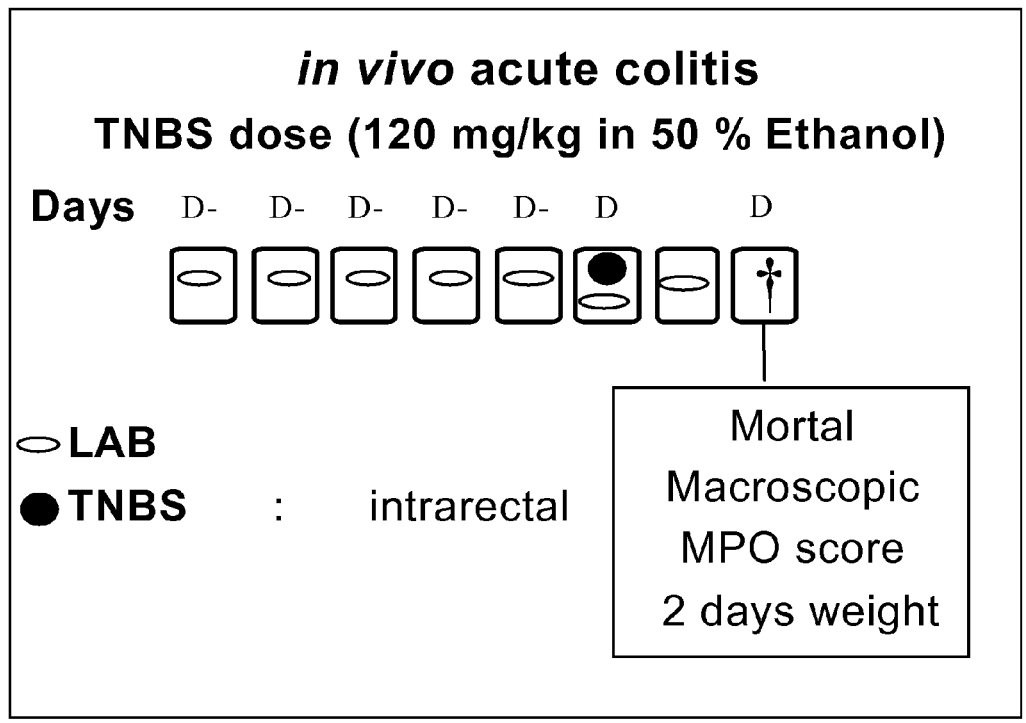
Figure 8:
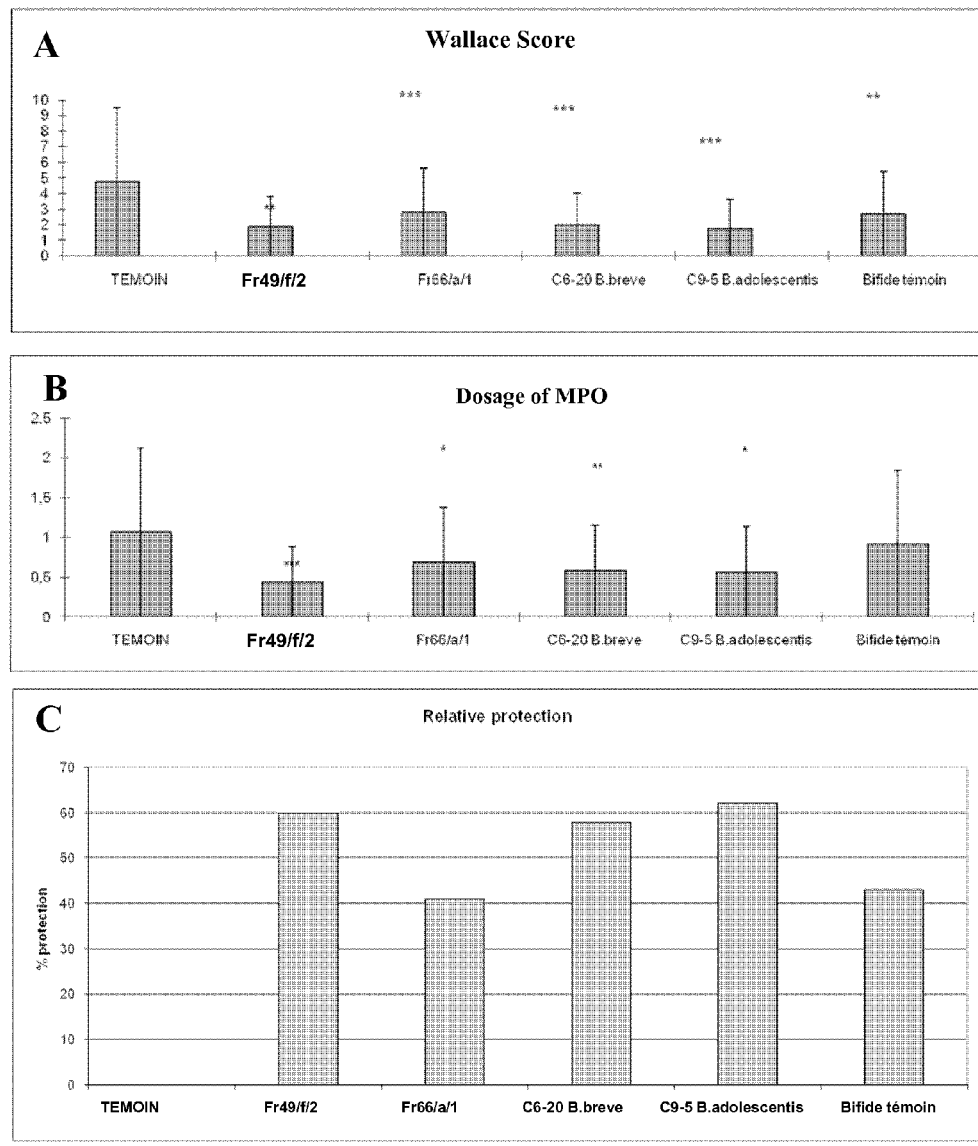

FIG. 2A—shows an alignment comparing the GC61 consensus sequence for the 16S rRNA gene (indicated as sequence no 1 in this figure) with those of other known Bifidobacterium species, indicating the % homology/identity between them. A consensus between the different species compared is shown by a sequence of characters which, according to the situation encountered in a given position, will include:

"•" if the character has a majority representation>=20%
":" If the character has a majority representation>=40%
"+" If the character has a majority representation>=60%
"*" If the character has a majority representation>=80%
the character itself, if it is the same for all sequences. This consensus sequence is designated as "C" in this figure;

FIG. 2B—shows a consensus tree of GC61 and the closest phylogenetically related Bifidobacterium species. The numbers on the branches indicate the number of times the partition of the species into the two sets which are separated by that branch occurred among the trees, out of 1.00 trees (trees had fractional weights);

FIG. 3—shows a consensus sequence of the hsp60 gene (Sequence ID No: 5) sequenced from the GC61 strains Fr 41/2, Fr49/f/2 and Fr101/h/8. The underlined bases correspond to PCR primers (Sequence ID Nos: 6 and 7), and highlighted bases correspond to the sequence of a probe (Sequence ID No: 8) specific to the GC61 species;

Figure 4:
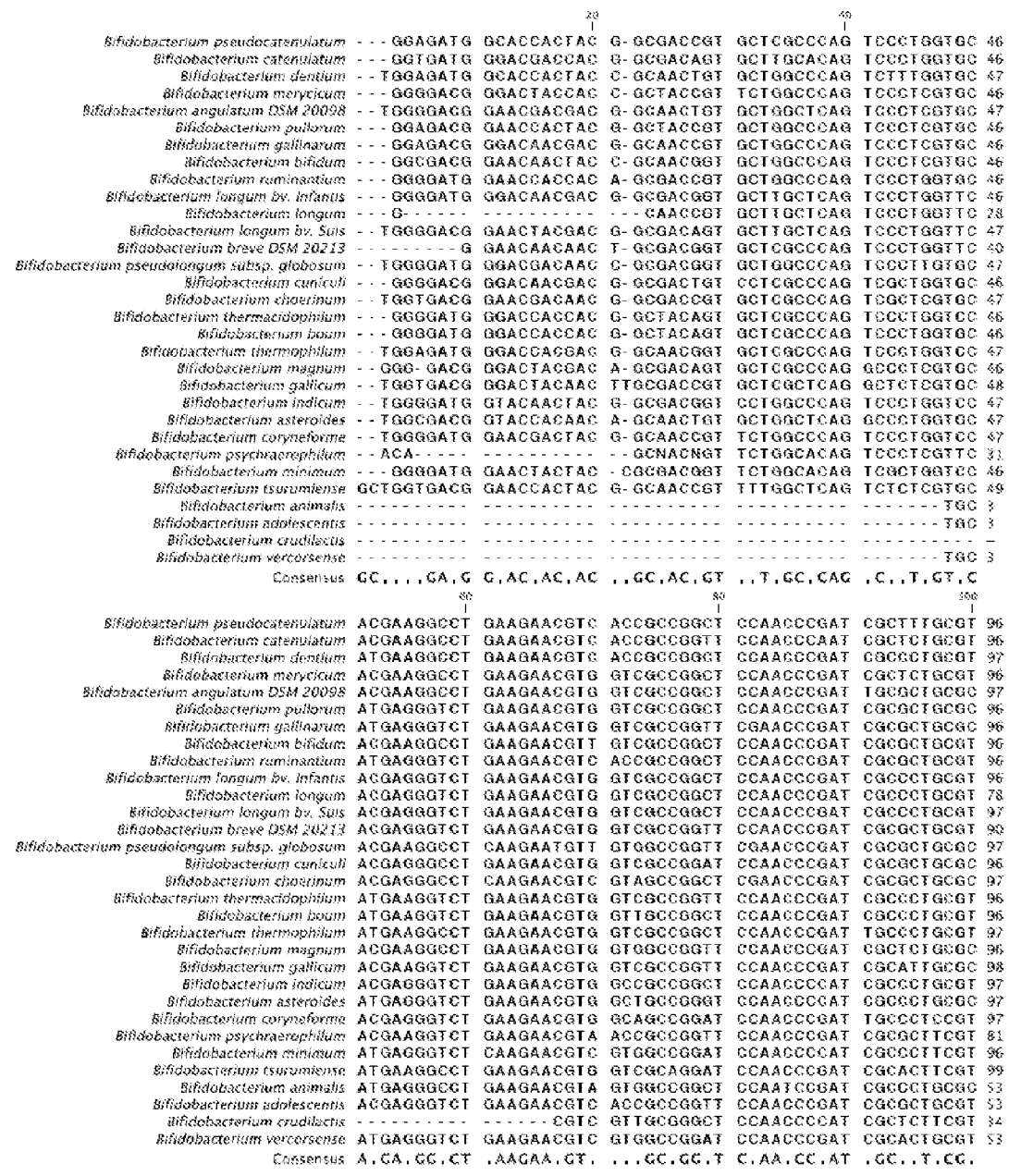
Figure 4:
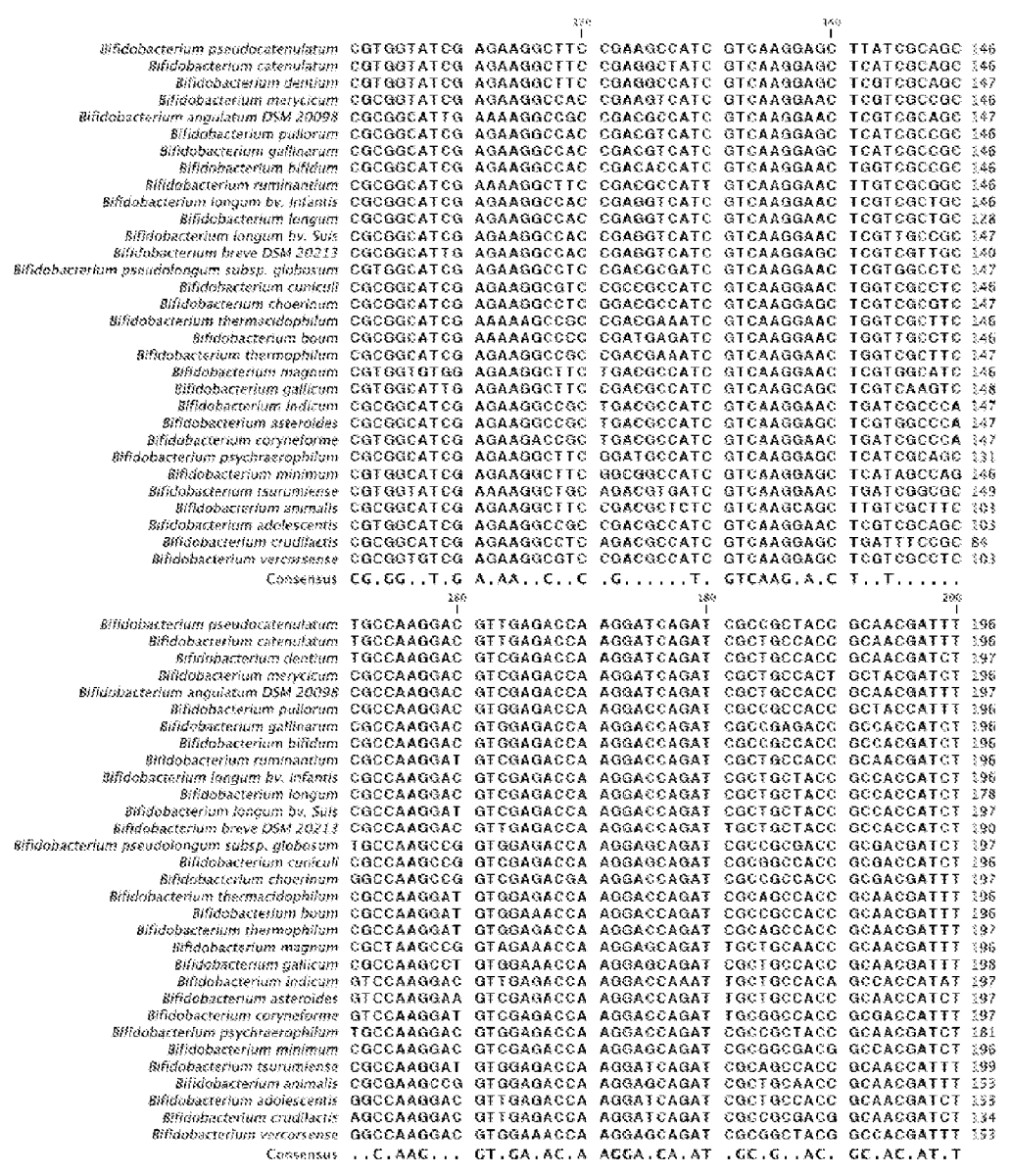

FIG. 4—shows an alignment of an hsp60 partial gene sequence from the GC61 group bacterium Bifidobacterium vercorsense, with closely related sequences in other bifidobacterium species found on Genbank (PubMed-BLAST). The partial hsp60 gene sequence from Bifidobacterium vercorsense is identical to the consensus sequence of the hsp60 gene referred to in FIG. 3;

FIG. 5—shows the experimental procedure used to study the effect on IFNγ, IL-10 and IL-12 in peripheral blood mononuclear cells (PBMCs) when stimulated with various bacterial isolates;

FIGS. 6A-D—show the effect on IFNγ, IL-10 and IL-12 levels in peripheral blood mononuclear cells when stimulated with various bacterial isolates including FR49/f/2 (strain C), FR101/H/8 (strain F), FR39/1 (strain I), FR41/2 (strain M) and FR66/E/1 (strain N);

FIG. 6A—shows induction of IFNγ; FIG. 6B—shows induction of IL-12; FIG. 6C—shows induction of IL-10; FIG. 6D—shows values of IL-10/IL-12; Souche=Strain, Temoin=control;

FIG. 7—illustrates the design of a standard bacterial interventional study for TNBS (2,4,6-trinitrobenzene sulfonic acid) induction of acute colitis; and FIGS. 8A-C—show the results of the study of TNBS induction of acute colitis; FIG. 8A—shows Wallace Scores for different strains; FIG. 8B—shows dosage of MPO for different strains; FIG. 8C—shows relative protection by strains. TEMOIN=control, Bifide témoin=control *Bifidobacterium*.

PHENOTYPE CHARACTERISTICS OF BIFIDOBACTERIUM GC61

*Bifidobacterium* GC61 has been phenotypically characterised and identified by numerical analysis (classification based on unweighted average linkage and Hartigan's clustering methods). No other type or reference strains belonging to another species of the *Bifidobacterium* genus has been identified which shares the characteristics of the GC61 group.

The biochemical characteristics which differentiate the GC61 group from other species, such as *B. crudilactis* (Delcenserie V., et al. *Systematic and Applied Microbiology* (2007) 30, 381-389) and *B. psychraerophilum* which are considered to be the closest phylogenetically related species, are presented in Table 1. Table 1 shows differential phenotypic characteristics between GC61 (13 strains), *B. crudilactis* (10 strains), *B. crudilactis* LMG 23609T, and *B. psychraerophilum* LMG 21775T.

TABLE 1

| Characteristics | GC61 (13 strains, % positive responses) | B. crudilactis (10 strains, % positive responses) | B. crudilactis LMG 23609$^T$ | B. psychraerophilum LMG 21775$^T$ (Simpson et al., 2004) |
|---|---|---|---|---|
| Acidification of: | | | | |
| L-arabinose | 100 | 0 | − | + |
| D-xylose | 0 | 10 | − | + |
| α-methyl-D-mannoside | 0 | 0 | − | + |
| N-acetylglucosamine | 0 | 0 | − | + |
| Salicin | 85 | 20 | − | + |
| Lactose | 100 | 100 | + | − |
| Melezitose | 0 | 10 | − | + |
| glycogen | 92 | 10 | − | − |
| Enzymatic tests: | | | | |
| α-arabinosidase | 100 | 0 | − | + |
| glycine arylamidase | 38 | 100 | + | + |
| Growth temperature range | 10° C.$^a$-41° C.$^b$ | 5° C.-45° C. | 4° C.-45° C. | 4° C.-42° C. |
| Minimum growth pH$^c$ | NT | | | 4.5 |
| DNA G + C content (mol %) | 61.1 (6 strains) (SD = 0.67) | 55.2 (9 strains) (SD = 0.83) | 56.4 (4 experiments) (SD = 0.60) | 59.2 (HPLC, Simpson et al., 2004) 55.7 (Tm$^d$) |

Legend of Table 1:
$^a$growth within 14 days;
$^b$within 8 days;
$^c$within 48 h;
$^d$mean of 2 experiments performed in the laboratory;
NT, not tested on all strains DNA-DNA Hybridization DNA-DNA reassociation levels across the entire bacterial genome of GC61 strains and other *Bifidobacterium* species and of *Aeriscardovia aeriphila* are between 3 and 28% (as illustrated in Table 2). Within the GC61 group (GC61 strains FR49/f/2, MarV3/22, FR39/1, MarV4/2, FR101/h/8, MarV1/5, FR66/e/1, MarC1/13, MarF/3, PicD/1, FR70/g/2 and FR47/2 were compared to the GC61 strain FR41/2) DNA-DNA reassociation levels of from 80% to 100% are observed.

DNA-DNA reassociation levels were determined using the spectrophotometric method for determining renaturation rates described by De Ley et at (*J Biochem* (1970) 12 133-142), slightly modified in hybridisation temperature (Gavini et al. *Ecology in Health and Disease* (2001) 12 40-45). The determinations were performed at 63.7° C. ($T_m$−25° C. according to the G+C content of the strain FR41/2), using a Cary 100 spectrophotometer (Varian) with a temperature controller (Peltier System, Varian).

TABLE 2

DNA-DNA relatedness (%) between DNAs of FR41/2 and *Bifidobacterium* and *Aeriscardovia aeriphila* type strains.

| Species/Collection and reference no. | % DNA-DNA relatedness with FR41/2 |
|---|---|
| FR49/f/2; MarV3/22 | 100 |
| FR39/1 | 95 |
| MarV4/2 | 94 |
| FR101/h/8; MarV1/5 | 93 |
| FR66/e/1 | 92 |
| MarC1/13 | 89 |
| MarF/3 | 88 |
| PicD/1 | 86 |
| FR70/g/2 | 84 |
| FR47/2 | 80 |
| *B. adolescentis* CCUG[a] 18363 | 24 |
| *B. angulatum* DSM 20098 | 18 |
| *B. animalis* subsp. *animalis* NCFB 2242 | 21 |
| *B. animalis* subsp. *animalis* ATCC 27674 | NT |
| *B. asteroides* DSM 20089 | 23 |
| *B. bifidum* DSM 20082 | NT |
| *B. bifidum* BS98[b] | 11 |
| *B. boum* DSM 20432 | 14 |
| *B. breve* NCFB 2257 | 6 |
| *B. catenulatum* CCUG 18366 | 15 |
| *B. choerinum* DSM 20434 | 21 |
| *B. coryneforme* DSM 20216 | 25 |
| *B. cuniculi* DSM 20435 | 12 |
| *B. crudilactis* LMG 23609 | 10 |
| *B. crudilactis* FR59/b/2 | NT |
| *B. crudilactis* FR47/3 | NT |
| *B. dentium* CCUG 18367 | 12 |
| *B. gallicum* DSM 20093 | 19 |
| *B. gallinarum* ATCC 33777 | 19 |
| *B. gallinarum* ATCC 33778 | NT |
| *B. indicum* DSM 20214 | 17 |
| *B. indicum* ATCC 25913 | NT |
| *B. longum* type *infantis* DSM 20088 | NT |
| *B. longum* type *longum* NCTC 11818 | 14 |
| *B. longum* type *suis* SU 859 | 18 |
| *B. longum* type *suis* ATCC 27532 | NT |
| *B. magnum* DSM 20222 | 10 |
| *B. magnum* ATCC 27681 | NT |
| *B. merycicum* RU 915 B | 21 |
| *B. minimum* DSM 20102 | 8 |
| *B. pseudocatenulatum* DSM 20438 | 18 |
| *B. pseudolongum* subsp. *globosum* RU 224 | 23 |
| *B. pseudolongum* subsp. *globosum* ATCC 25864 | NT |
| *B. pseudolongum* subsp. *pseudolongum* MB7 | 25 |
| *B. pseudolongum* subsp. *pseudolongum* DSM 20094 | NT |
| *B. psychraerophilum* LMG 21775 | 27 |
| *B. pullorum* DSM 20433 | NT |
| *B. ruminantium* RU 687 | 20 |
| *B. saeculare* DSM 6531 | 13 |
| *B. scardovii* DSM 13734 | 3 |
| *B. subtile* DSM 20096 | 15 |
| *B. subtile* ATCC 27683 | NT |
| *B. thermacidophilum* subsp. *thermacidophilum* LMG 21395 | 17 |
| *B. thermacidophilum* subsp. *porcinum* LMG 21689 | 22 |
| *B. thermophilum* MB1 | 4 |
| *B. thermophilum* DSM 20212 | NT |
| *Aeriscardovia aeriphila* LMG 21773 | 28 |

Legend of Table 2:
[a]International collection type strain came from: ATCC, American Type Culture Collection, Rockville, Maryland, USA; CCUG, Culture Collection of University of Göteborg, Sweden; DSMZ, Deutsche Sammlung von Mikroorganismen and Zellkulturen GmbH, Göttingen, Germany; LMG, Laboratorium voor Microbiologie, Universiteit Gent, Belgium, NCFB, National Collection of Food Bacteria, Shinfield, Reading, Berks, England; NCTC, National Collection of Type Cultures, Central Public Health Laboratory, London, England; RU, SU and MB, *B. Biavati*, Bologna, Italy;
[b]strain isolated from human faeces sharing 100% DNA-similarity with *B. bifidum* DSM 20082;
NT, not tested.

16S rRNA Gene Sequencing

The 16S rRNA gene of the GC61 group strains FR41/2, FR49/f/2 and of FR101/h/8 was amplified and sequenced (FIG. 1A). By using BLAST analysis the percentage sequence identity between the consensus sequence for the 16S rRNA gene from the GC61 strains FR41/2, FR49/f/2 and of FR101/h/8 (see FIG. 1B) and the 16S rRNA gene sequence from other *Bifidobacterium* species was determined (FIG. 2A). The results are summarised in Table 3.

TABLE 3

| Strains and reference no. | Sequences producing significant alignments | Identities | Length of alignment |
|---|---|---|---|
| FR41/2, FR49/f/2, FR101/h/8, consensus sequence (FIG. 1B) | AY174108 *Bifidobacterium psychroaerophilum* LMG21775 | 95.45% | 1428 pb |
| | AY952448 *Bifidobacterium crudilactis* FR/59/b/2 | 95.23% | 1384 pb |
| | AY174103 *Bifidobacterium minimum* | 94.77% | 1416 pb |
| | D89378 *Bifidobacterium subtile* DSM20096 | 94.56% | 1453 pb |
| | D86196 *Bifidobacterium pullorum* JCM1214 | 94.48% | 1413 pb |
| | D86188 *Bifidobacterium indicum* JCM1302 | 94.43% | 1453 pb |
| | D86191.1 *Bifidobacterium gallinarum* JCM6291 | 94.3% | 1453 pb | hsp60 Sequencing

The hsp60 gene was amplified and sequenced from the strains FR41/2, FR49/f/2 and FR101/h/8 of the GC61 group. The sequences were compared and the consensus sequence shown in FIG. 3 was identified. This consensus sequence reflects a partial sequence of the hsp60 gene. Using the consensus sequence specific PCR primers and a specific probe for GC61 strains were selected (FIG. 3). The primers and/or probe allow real-time PCR to be used to detect GC61 strains.

BLAST analysis was used to identify other *Bifidobacterium* species which produced significant alignment with the hsp60 gene consensus sequence of FIG. 3.

Table 4 and FIG. 4 show the homology/percent identity between a partial gene sequence (212 pb) of the hsp60 gene from the GC61 group bacterium *Bifidobacterium vercorsense* (see FIG. 3) and the corresponding gene from different *Bifidobacterium* species (see FIG. 4).

TABLE 4

| Species | Reference | Identities | Length of alignment |
|---|---|---|---|
| Bifidobacterium adolescentis | AF210319 | 87% | 212 b |
| Bifidobacterium pullorum | AY004278 | 86% | 212 b |
| Bifidobacterium gallinarum | AY004279 | 86% | 212 b |
| Bifidobacterium dentium | AF240572 | 86% | 212 b |
| Bifidobacterium choerinum | AY013247 | 86% | 212 b |
| Bifidobacterium ruminantium | AF240571 | 86% | 212 b |
| Bifidobacterium cuniculi | AY004283 | 86% | 212 b |
| Bifidobacterium minimum | AY004284 | 86% | 210 b |
| Bifidobacterium thermacidophilum | AY166558 | 86% | 210 b |
| Bifidobacterium infantis | AY166569 | 86% | 207 b |
| Bifidobacterium longum | AY835622 | 86% | 207 b |
| Bifidobacterium boum | AF240566 | 85% | 212 b |
| Bifidobacterium merycicum | AY004277 | 85% | 212 b |
| Bifidobacterium bifidum | AY004280 | 85% | 212 b |
| Bifidobacterium pseudocatenulatum | AY004274 | 85% | 212 b |
| Bifidobacterium gallicum | AF240575 | 85% | 212 b |
| Bifidobacterium suis | AY013248 | 85% | 207 b |
| Bifidobacterium breve | AF240566 | 85% | 207 b |
| Bifidobacterium psychraerophilum | AY339132 | 85% | 204 b |
| Bifidobacterium crudilactis | Fr54/e/1 (lab isolate) | 85% | 193 b |
| Bifidobacterium thermophilum | AF240567 | 84% | 212 b |
| Bifidobacterium magnum | AF240569 | 84% | 212 b |
| Bifidobacterium pseudolongum globosum | AF286736 | 84% | 212 b |
| Bifidobacterium angulatum | AF240568 | 84% | 212 b |
| Bifidobacterium animalis | AY488183 | 84% | 212 b |
| Bifidobacterium catenulatum | AY166565 | 83% | 212 b |
| Bifidobacterium tsurumiense | AB244755 | 82% | 212 b |
| Bifidobacterium indicum | AF240574 | 82% | 207 b |
| Bifidobacterium asteroides | AF240570 | 81% | 212 b |
| Bifidobacterium coryneforme | AY004275 | 80% | 207 b |

Specific Detection of GC61 by PCR

A real-time PCR (polymerase chain reaction) assay was developed in order to detect specifically the GC61 group.

DNA was prepared using the Wizard® genomic DNA purification kit from Promega™. 1 ml of bacterial culture was centrifuged for 2 minutes at 13000×g. The supernatant was discarded and the pellet was resuspended in 480 µl EDTA, 60 µl of lysosyme, and 120 µl of cellular lysis solution and incubated for 45 minutes at 37° C. After centrifugation, 600 µl of nuclei lysis solution was added to the pellet followed by incubation for 5 min at 80° C. When cooled, 200 µl of protein lysis solution was added followed by vortexing. The resultant suspension was then incubated for 5 min on ice and centrifuged for 5 min at 13000×g. The supernatant was transferred to a clean tube containing 600 µl of isopropanol and the tube was then centrifuged. The supernatant was decanted and 600 µl of 70% ethanol was added and the tube was centrifuged. The ethanol was aspirated and the pellet was air-dried for 10 min. Finally, the DNA pellet was rehydrated in 100 µl of rehydration solution overnight at 4° C.

Amplification reaction mixtures contained 10 to 50 ng of DNA, 12.5 µl of TaqMan universal PCR Mastermix (Applied Biosystems, USA), 900 nM of each primer, 200 nM of fluorogenic probe in a total volume of 25 µl. The primers used were: 5'TCCGACGCCATCGTCAA 3' (Sequence ID No: 6) and 5'-CGATCTGCTCCTTGGTTTCC-3' (Sequence ID No: 7). The probe sequence was 5'-TCGTCGCCTCGGC-3' (Sequence ID No: 8). As a control, a reaction mix was prepared which lacked a DNA sample. Sequences of the primers and probe are presented in FIG. 3.

For amplification a thermal cycler was programmed as follows: 50° C. for 2 min, 95° C. for 10 min, and then 40 cycles of two-temperature PCR (95° C. for 15 s and 60° C. for 60 s) and detection was carried out on an ABI Prism 7000 sequence detection system (Applied Biosystems, Foster city, USA). The PCR results for the samples were expressed as deltaRn (relative sensitivity) fluorescence signal.

A sample was considered as positive when the Ct value was lower than 35 for a relative fluorescence (Rn level) value of at least 1.0.

In the PCR experiments performed all the GC61 group isolates were positive and all the other *Bifidobacterium* (*animalis, thermophilum, choerinum, globosum, pseudolongum, merycicum, ruminatum, minimum, cuniculi, adolescentis, bifidum, breve, dentium, longum, pseudocatenulatum* and *crudilactis*) species tested were negative in this assay.

Gastro-Intestinal Resistance of GC61 Strains

The FR/49/f/2 and FR/41/2 strains from the *Bifidobacterium* GC61 group were tested in this part of the study.

The materials used include:

MRS: Man Rogosa Sharpe medium (Oxoid GmbH, Wesel, Allemagne),

Gastric juice: solution of pepsin (0.3% w/v) (P7000 Sigma) in NaCl-water (0.5% w/v) adjusted to pH 2 and 3 with HCl.

Pancreatic juice: solution of pancreatine USP (1 gr/l) (P1500 Sigma) in NaCl-water (0.5% w/v) adjusted to pH 8 with NaOH.

Bile salt: MRS medium with 0.3%, 0.5% and 1% (w/v) bile (LP0055, Oxoid).

Buffer solution: $K_2HPO_4$ 50 mM

Study at pH 2 and 3—two stains of GC61, FR/49/f/2 and FR/41/2, were inoculated in MRS broth and incubated anaerobically at 37° C. for 36 hours. After centrifugation, the bacteria were resuspended in NaCl 0.5% solution adjusted to pH 2 or pH 3. The suspension was anaerobically incubated at 37° C. and samples taken each hour for 5 hours. Samples were plated using a spiral plater on MRS agar medium (Don Whitley Scientific LTD., Shipley, West Yorkshire, UK). Plates were incubated for 72 hours at 37° C. before counting the number of colonies. All the manipulations were performed in an anaerobic cabinet. Manipulations were realised in triplicate.

Study in gastric juice at pH 2 and 3—the two stains (FR/49/f/2 and FR/41/2) were inoculated in MRS broth and incubated anaerobically at 37° C. for 36 hours. After centrifugation, the bacteria were resuspended in gastric juice solution adjusted to pH 2 or pH 3. The suspension was anaerobically incubated at 37° C. and samples taken each hour for 5 hours. Samples were plated using a spiral plater on MRS agar medium (Don Whitley Scientific LTD., Shipley, West Yorkshire, UK). Plates were incubated for 72 hours at 37° C.

before counting the number of colonies. All the manipulations were performed in an anaerobic cabinet. Manipulations were realised in triplicate.

Study in pancreatic juice at pH 8—the two stains (FR/49/f/2 and FR/41/2) were inoculated in MRS broth and incubated anaerobically at 37° C. for 36 hours. After centrifugation, the bacteria were resuspended in pancreatic juice solution adjusted to pH 8. The suspension was anaerobically incubated at 37° C. and samples taken each hour for 5 hours. Samples were plated using a spiral plater on MRS agar medium (Don Whitley Scientific LTD., Shipley, West Yorkshire, UK). Plates were incubated for 72 hours at 37° C. before counting the number of colonies. All the manipulations were performed in an anaerobic cabinet. Manipulations were realised in triplicate.

Study in MRS medium with bile salts—the two stains (FR/49/f/2 and FR/41/2) were inoculated in MRS broth and incubated anaerobically at 37° C. for 36 hours. After centrifugation, the bacteria were resuspended in MRS medium with 0.3%, 0.5% and 1% bile salts The suspension was anaerobically incubated at 37° C. and samples taken at the beginning of the experiment and after 48 hours. Samples were plated using a spiral plater on MRS agar medium (Don Whitley Scientific LTD., Shipley, West Yorkshire, UK). Plates were incubated for 72 hours at 37° C. before counting the number of colonies. All the manipulations were performed in an anaerobic cabinet. Manipulations were realised in triplicate.

Results

The resistance to gastro-intestinal conditions of some isolates (Fr41/2 and Fr49/f/2) was evaluated in vitro. The results (in log 10 cfu change) shown in Tables 5 and 6 confirm the potential probiotic use of GC61.

Table 5 shows the resistance of Fr49/f/2 and Fr41/2 strains of GC61 to pepsin solutions at pH 2 and pH 3 and pancreatic enzymes at pH 8 after 5 hours at 37° C. in anaerobic cabinet. The results are expressed in log 10 reduction after the incubation period. A good resistance was observed at pH3 and with pancreatic enzymes (less than 1 log 10 cfu reduction).

TABLE 5

| Strains | Physiological water | | Pepsin | | Pancreatic enzymes |
|---|---|---|---|---|---|
| | pH 2 | pH 3 | pH 2 | pH 3 | pH 8 |
| Fr49/f/2 | >−3 | 0 | >−4.8 | −0.2 | −0.2 |
| Fr41/2 | >−3 | 0 | −3.1 | −0.4 | −0.5 |

Table 6 shows resistance of Fr49/f/2 and Fr41/2 strains to bile salts in MRS medium after 48 hours at 37° C. in anaerobic cabinet. The results are expressed in log 10 reduction or growth after the incubation period. A low number reduction was observed at pH3 and with 0.3% bile salts (less than 2 log 10 cfu reduction).

TABLE 6

| | Bile Salts | | | |
|---|---|---|---|---|
| Strains | 1% | 0.5% | 0.3% | 0% |
| Fr49/f/2 | −3.1 | −2.6 | −1 | +1.1 |
| Fr41/2 | −3.5 | −3.1 | −1.8 | +2 |

Gastro-Intestinal Immunity Modulation

It was also determined that some isolates of the GC61 group have interesting immunomodulatory effects by modulating cytokine levels.

IL-10 is a cytokine produced by T cells, B cells, monocytes and macrophages. IL-10 augments the proliferation and differentiation of B cells into antibody secreting cells. IL-10 exhibits mostly anti-inflammatory activities and may be an important negative regulator of connective tissue destruction seen in chronic inflammatory diseases.

IL-12 is a cytokine produced primarily by antigen presenting cells, such as macrophages, early in the inflammatory cascade. It is a potent inducer of IFNγ production and is an activator of natural killer cells. Inhibition of IL-12 in vivo may have some therapeutic value in the treatment of inflammatory disorders, such as multiple sclerosis.

IFNγ is primarily a product of activated T lymphocytes and synergizes with other cytokines resulting in a more potent stimulation of monocytes, macrophages, neutrophils and endothelial cells.

To test the effect of GC61 on IL-10, IL-12 and IFNγ production, peripheral blood mononuclear cells (PBMCs) were isolated from healthy donors (n=5) by density gradient centrifugation. The isolated peripheral blood mononuclear cells were then stimulated with bacterial isolates, including the GC61 probiotic bacterial isolates FR49/f/2, FR101/h/8, FR39/1, FR41/2, and FR66/e/1, for a 72 hour period at 37° C. The supernatants were then collected, centrifuged and assayed for IL-10, IL-12 and IFNγ levels by ELISA.

Method

The *Bifidobacterium* strains, including FR49/f/2, FR101/h/8, FR39/1, FR41/2, and FR66/e/1, were cultivated in MRS medium (Difco) supplemented with cysteine (Sigma at 0.5 g/l) in anaerobic jars with gaspacks (GENbag Biomerieux). All strains were found to be pure.

Subcultures of these pure strains were used in all further experimentations and were preserved as glycerol cultures at −80° C. for back-up and quality control.

PBMC Preparation

As illustrated in FIG. 5, fresh human blood, obtained from healthy subjects, was diluted at a 1:2 ratio with PBS-Ca (GIBCO) (test tube A in FIG. 6) and purified on a Ficoll gradient (GIBCO). After centrifugation at 400×g for 30 min at 20° C. the peripheral blood mononuclear cells (PBMC's) formed an interphase ring layer in the serum (test tube B in FIG. 5). The PBMC's were aspirated carefully, suspended to a final volume of 50 ml using PBS-Ca and washed three times in the same buffer with centrifugation steps at 350×g for 10 min at 20° C.

PBMC's were subsequently resuspended using complete RPMI medium (GIBCO), supplemented with 10% w/v foetal calf serum (inactivated at 56° C. for 30 min), 1% w/v L-glutamine (GIBCO), and gentamycin (150 µg/ml) (GIBCO). PBMC's were counted under the microscope and adjusted to a concentration of $2 \times 10^6$ cells/ml and distributed (in 1 ml aliquots) in 24-well tissue culture plates (Corning, Inc.).

Bacteria Preparation

*Lactobacillus* or *Bifidobacterium* cultures were grown overnight and then were washed twice with PBS buffer, pH 7.2, before being resuspended in PBS at a concentration of $2 \times 10^9$ cfu/ml. Table 7 details the bacterial strains studied, which includes the GC61 isolates FR49/f/2 (=strain C), FR101/h/8 (=strain F), FR39/1 (=strain I), FR41/2 (=strain M), and FR66/E/1 (=strain N). As well as GC61 strains (strains A to P), strains of other *Bifidobacterium* species (strains Q to Z) were also studied.

TABLE 7

| Strain no. IPL | Original no. | Taxonomic group |
|---|---|---|
| strain A | FR62/b/3 | Group 1 |
| strain B | FR56/a/3 | Group 1 |
| strain C | FR49/f/2 | Group GC61 |
| strain D | FR55/d/2 | Group 1 |
| strain E | FR54/e/1 | Group 1 |
| strain F | FR101/h/8 | Group GC61 |
| strain G | FR59/b/2 | Group 1 |
| strain H | FR57/h/4 | Group 1 |
| strain I | FR39/1 | Group GC61 |
| strain J | FR35/5 | Group 1 |
| strain K | FR50/f/4 | Group 1 |
| strain L | FR60/h/1 | Group 1 |
| strain M | FR41/2 | Group GC61 |
| strain N | FR66/e/1 | Group GC61 |
| strain O | FR51/h/1 | Group 1 |
| strain P | FR66/a/1 | Group 1 |
| strain Q | | C 4A *B. adolescentis* |
| strain R | | C 3-12 *B. adolescentis* |
| strain S | | C 5-19 *B. adolescentis* |
| strain T | | C 1-7 *B. longum* |
| strain U | | C2-2 *B. pseudocatenulatum* |
| strain V | | C 6-20 *B. breve* |
| strain W | | C 9-4 *B. dentium* |
| strain X | | C 9-5 *B. adolescentis* |
| strain Y | | C 12-19 *B. dentium* |
| strain Z | | C 11-15 *B. dentium* |

PBMC Incubation

10 μl of the bacterial suspensions were then transferred into the wells containing the PBMCs. The plates were then incubated at 37° C. in a 5% $CO_2$/95% air atmosphere. After 24 h incubation the supernatant was aspirated, centrifuged at 2000 rpm (Eppendorf model) and the supernatant removed and stored at −20° C. As a control (Temoin) the procedure was performed using a bacteria free buffer instead of the bacterial suspension.

Cytokine Quantification

The level of the pro-inflammatory/Th1 cytokine IFNγ, of IL-12 and of the anti-inflammatory regulatory cytokine IL-10 was determined in the supernatant removed from the treated PMBCs.

Cytokine expression levels were determined by ELISA. ELISA plates were coated with one or more specific anti-cytokine antibodies (in an overnight procedure) and the antibody was blocked with PBS/BSA 1%.

The cytokines were detected and quantified using a streptavidin reaction. The commercial kits of Pharmingen containing TMB (tetramethylbenzidine) were used according to the manufacturer's instructions.

Results

The results of the cytokine analysis are presented in FIGS. 6A to 6D. Each data point is the mean of the analysis of 5 blood samples, each from different donors.

As can be seen from FIG. 6C the FR49/f/2 (strain C), FR39/1 (strain I), FR41/2 (strain M) and FR66/E/1 (strain N) strains all significantly induced IL-10 production following co-incubation with peripheral blood mononuclear cells. The FR101/H/8 (strain F) strain did not significantly alter IL-10 levels compared to the controls.

As can be seen from FIG. 6B the FR49/f/2 (strain C) strain induced no stimulation of IL-12 production and showed an interesting anti-inflammatory effect as indicated by the high level of the IL-10/IL-12 coefficient (FIG. 6D). The level observed for FR49/f/2 is as high as the best *Bifidobacterium* species previously tested.

All the tested strains except the FR49/f/2 strain induced IFNγ production.

In conclusion, the FR49/f/2 strain has a good profile for use in anti-inflammatory probiotic applications.

Evaluation of FR49/f/2 (Strain C) and FR66/a/1 (Strain P) Strains for their Immuno-Modulatory Potential in a Model of Colitis Strain C (FR49/f/2) from GC61 group and strain P (FR66/a/1) from the non-GC61 group 1 showed opposite properties in PBMC tests (FIG. 6) and were further studied to evaluate their immuno-modulatory potential in an animal model of colitis.

Strains V (C 6-20) and X (C 9-5) were used as positive controls, as they have a high IL-10/IL-12 ratio in in vitro studies.

Chemical Reagents

Chemicals and reagents were purchased from Sigma-Aldrich Chemical, France unless indicated otherwise.

Animals

Animal experiments were performed in an accredited establishment (number A59107; animal facility of the Institut Pasteur de Lille, France) according to French government guidelines (number 86/609/CEE). Conventional adult female BALB/C mice (aged 7/8 weeks), with homogenous flora, breast-fed (Felasa, 1994—(Federation of European Laboratory Animal Science Associations). *Laboratory Animals*, 28: 1-12) and maintained under specific pathogen-free (SPF) conditions, were purchased from Iffa Credo (Saint-Germain sur l'Arbresle, France). Mice were group housed (8-10/cage) and kept under filter top hoods behind a barrier under SPF conditions. Mice had free access to tap water and rodent chow and underwent at least one week of acclimatization before any intervention. Groups of 10 mice were used for each experimental group.

Preparation of Bacterial Cultures and Administration to Mice

Strains investigated were grown as described above in the PBMC method. $10^8$ bacteria were used per daily administration.

TNBS Induction of Acute Colitis and Study Design

The design of the standard bacterial interventional study is represented in FIG. 7. Briefly, bacterial suspensions were given to mice from day −5 before induction of colitis to day +1 after induction of colitis on day 0. Mortality rate, macroscopic scores of inflammation, body weight and MPO (myeloperoxidase activity) were assessed 48 h after colitis induction. Mice were anesthetized with 3 mg of ketamine (Imalgene 1000; Mérial Lyon, France), 46.7 μg of diazepam (Valium, Roche Diagnostics) and 15 μg of atropine (Aguettant Laboratory, Lyon, France) dissolved in 0.9% NaCl. TNBS (Fluka, France) at a dose of 120 mg/kg of body weight was dissolved in 0.9% NaCl/ethanol (50/50 v/v) and 50 μl were administered intra-rectally at 4 cm proximal to the anus, using a 3.5 F catheter (EO 3416-1; Biotrol, Chelles, France). "Negative control" mice received only 50% ethanol ("Ethanol-mice"). "Positive control" mice (also referred to as "TNBS-control" or "TNBS-treated" mice) were fed only with $NaHCO_3$ buffer, in comparison with "treated" mice, which were additionally administered an amount of bifidobacteria. Animals were sacrificed by cervical dislocation 2 days after TNBS administration. Mice were weighed prior to TNBS administration and upon sacrifice.

Macroscopic Assessment of Colitis

The colon was dissected free from fat and mesentery, before being removed and carefully opened and cleaned with PBS. Colonic damage and inflammation were assessed according to the Wallace criteria (Wallace et al. 1989, *Gastroenterology*. 96(1):29-36—summarized in Table 9). These criteria for macroscopic scoring (scores ranging between 0 and 10) have been well established in both rats and mice studies, and reflect (i) the intensity of inflammation, (ii) the thickening of the colon mucosa and (iii) the extent of the ulceration (Table 9).

TABLE 9

| Wallace Score | Description of symptoms |
|---|---|
| 0 | Normal appearance of the colon |
| 1 | Focal hyperhemia, slight thickening, no ulcers |
| 2 | Hyperhemia, prominent thickening, no ulcers |
| 3 | Ulceration with inflammation at one site |
| 4 | Ulceration with inflammation at two or more sites |
| 5 | Major sites of damage extends > 1 cm |
| 6-10 | When area of damage extends > 2 cm, the score is increased by 1 for each additional cm of involvement. |

Myeloperoxidase (MPO) Activity

The activity of the enzyme MPO, a marker of polymorphonuclear neutrophil primary granules, was determined in the proximal colon tissue according to Bradley et al, (1982. *J Invest Dermatol.* 78(3):206-9). Immediately after sacrifice, a colonic sample (1 cm long) was taken at 3 cm from the ceco-colonic junction. Samples were suspended in a potassium phosphate buffer (50 mmol/L, pH 6.0) and homogenized in ice using a polytron. Three cycles of freezing and thawing were undertaken. Suspensions were centrifuged at 10,000×g for 15 min at 4° C. Supernatants were discarded and pellets were resuspended in hexadecyl trimethylammonium bromide buffer (HTAB 0.5%, w/v, in 50 mmol/l potassium phosphate buffer, pH 6.0), a detergent inducing release of MPO from the polymorphonuclear neutrophil primary granules. These suspensions were sonicated on ice, and again centrifuged for 15 min at 4° C. Supernatants obtained were diluted in potassium phosphate buffer (pH 6.0) containing 0.167 mg/ml of O-dianisidine dihydrochloride and 0.0005% of hydrogen peroxide ($H_2O_2$). MPO from human neutrophils (0.1 U/100 ml, Sigma) was used as a standard. Changes in absorbance at 450 nm, over 5 and 10 min, were recorded with a microplate spectrophotometer (ELX808, Bio-Tek Instrument, CA). One unit of MPO activity is defined as the quantity of MPO degrading 1mmol hydrogen peroxide/min/ml at 25° C. Results are given as mean +/− SEM.

Results

The degree of protection conferred by a bacterial strain is expressed herein as the "% relative protection" which refers to the % reduction of the mean macroscopic inflammation of treated mice in relation to the mean score of non-treated mice (TNBS-control group). The % relative protection is calculated as detailed below.

% relative protection=100×(average Wallace score "positive control" group−average Wallace score "treatment" group)/average Wallace score "positive control" group This calculation allows the comparison of groups of mice within and between experiments.

Applying this 'relative protection' to the average colitis level of each "positive control" group, also allows the elimination of inevitable Wallace score variations between independent experiments.

FIG. 8A-C and Table 10 shows the results obtained when 6 different groups of 10 mice were analysed.
    group 1: 10 TNBS treated mice (no bacteria)
    group 2: 10 TNBS treated mice (+ strain Fr 49/f/2)
    group 3: 10 TNBS treated mice (+ strain Fr 66/a/1)
    group 4: 10 TNBS treated mice (+ strain C6-20)
    group 5: 10 TNBS treated mice (+ strain C9-5)
    group 6: 10 TNBS treated mice (− contol *Bifidobacterium* strain)

TABLE 10

| | Score Walace | sem | student | Protection | |
|---|---|---|---|---|---|
| Group 1 - TNBS | 4.75 | 0.037 | | 0.00 | |
| Group 2 - C FR49/f/2 | 1.9 | 0.056 | 1.38 10exp-11 | 60.00 | **** |
| Group 3 - P FR66/a/1 | 2.8 | 0.161 | 0.000346 | 41.05 | *** |
| Group 4 - V B. breve C6-20 | 2 | 0.163 | 8.67 10exp-6 | 57.89 | **** |
| Group 5 - X B. adolescentis C9-5 | 1.8 | 0.147 | 1.01 10exp-6 | 62.11 | **** |
| Group 6 - Bifido ctrl | 2.7 | 0.211 | 0.0018 | 43.16 | ** |

As expected from the IL-10/IL-12 ratio, strain C (FR49/f/2) protected well in the colitis model.

Strain P (FR66/a/1), another non-GC61 group *Bifidobacterium*, also showed some protection.

The data presented demonstrates that some isolates of the GC61 group, and the FR49/f/2 strain in particular, have anti-inflammatory properties, supporting the assertion that they may be used as immunomodulatory agents.

The invention claimed is:

1. An isolated *Bifidobacterium* GC61 comprising SEQ ID NO: 1, SEQ ID NO: 2, SEQ ID NO: 3, or SEQ ID NO: 5.

2. An isolated *Bifidobacterium* strain which has DNA sequence homology across the entire bacterial genome of greater than about 80% to the isolated *Bifidobacterium* GC61 according to claim 1.

3. An probiotic composition comprising the isolated *Bifidobacterium* GC61 as defined in claim 1 and one or more acceptable excipients.

4. The probiotic composition as defined in claim 3 wherein said composition is a food product.

5. The probiotic composition as defined in claim 4 wherein said food product is a dairy based product selected from fermented milk, vegetable milk, soybean milk, butter, cheese and yoghurt.

6. A composition comprising the isolated *Bifidobacterium* GC61 as defined in claim 1 together with a further therapeutic agent or agents for the preparation of a medicament for the treatment of one or more of gastrointestinal diseases, Crohn's disease, ulcerative colitis, inflammatory disorders, immunodeficiency, inflammatory bowel disease, irritable bowel syndrome, cancer (particularly of the gastrointestinal and immune systems), diarrhoeal disease, antibiotic associated diarrhoea, paediatric diarrhoea, appendicitis, autoimmune disorders, multiple sclerosis, Alzheimer's disease, rheumatoid arthritis, coeliac disease, diabetes mellitus, organ transplant rejection, bacterial infections, viral infections, fungal infections, periodontal disease, urogenital disease, sexually transmitted disease, HIV infection, HIV replication, HIV associated diarrhoea, surgical associated trauma, surgical-induced metastatic disease, sepsis, weight loss, anorexia, fever control, cachexia, wound healing, ulcers, gut barrier function, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, psoriasis, acne vulgaris and/or cholesterol excesses.

7. A method for preparing a medicament for the treatment of inflammation in a mammalian subject comprising the step of combining the isolated *Bifidobacterium* GC61 as defined in claim 1 with a pharmaceutically acceptable excipient.

* * * * *

SEQUENCE LISTING

```
<160> NUMBER OF SEQ ID NOS: 8

<210> SEQ ID NO 1
<211> LENGTH: 1470
<212> TYPE: DNA
<213> ORGANISM: Bifidobacterium sp.

<400> SEQUENCE: 1
atcctggctc aggatgaacg ctggcggcgt gcttaacaca tgcaagtcga acgggatccg      60
aggcgcttgc gtctcggtga gagtggcgaa cgggtgagta atacgtgact aacctgcctc     120
atacatcgga atagctcctg gaaacgggtg gtaatgccga atgctccaac cttccgcatg     180
gatggttggg aaagcgttag cggtatgaga tggggtcgcg tcctatcagc ttgttggtgg     240
ggtgaaggcc caccaaggct tcgacgggta gccggcctga gagggtgacc ggccacattg     300
```

```
ggactgagat acggcccaga ctcctacggg aggcagcagt ggggaatatt gcacaatggg    360
cgaaagcctg atgcagcgac gccgcgtgcg ggatgaaggc cttcgggttg taaaccgctt    420
ttgattggga gcaagcgaga gtgagtgtac ctttcgaata agcaccggct aactacgtgc    480
cagcagccgc ggtaatacgt agggtgcaag cgttatccgg aattattggg cgtaaagagc    540
tcgtaggcgt tttgtcgcgt ctggtgtgaa agtccatcgc ttaacggtgg atctgcgccg    600
ggtacgggca ggctagagtg cgacagggga gactggaatt cccggtgtaa cggtggaatg    660
tgtagatatc gggaagaaca ccaatggcga aggcaggtct ctgggtcgtc actgacgctg    720
aggagcgaaa gcgtggggag cgaacaggat tagatacccct ggtagtccac gccgtaaacg    780
gtggatgctg gatgtgggc ccattccacg ggttccgtgt cggagctaac gcgttaagca    840
tcccgcctgg ggagtacggc cgcaaggcta aaactcaaag aaattgacgg ggcccgcac    900 aagcggcgga gcatgcggat taattcgatg caacgcgaag aaccttacct gggcttgaca    960
tgttcctgac ggccgcggag acgcggcttc ccttcggggc aggttcacag gtggtgcatg   1020
gtcgtcgtca gctcgtgtcg tgagatgttg ggttaagtcc cgcaacgagc gcaaccctcg   1080
ccttgtgttg ccagcacgtt atggtgggaa ctcgcaaggg accgccgggg ttaactcgga   1140
ggaaggtggg gatgacgtca gatcatcatg ccccttacgt ccagggcttc acgcatgcta   1200
caatggccgg tacaacggga tgcgacgcgg tgacgcggag cggatccctt aaaaccggtc   1260
tcagttcgga ttggagtctg caactcgact ccatgaaggc ggagtcgcta gtaatcgcga   1320
atcagcaacg tcgcggtgaa tgcgttcccg ggccttgtac acaccgcccg tcaagtcatg   1380
aaagtgggta gcacccgaag ccggtggcct aaccttttgg ggggagccgt ctaaggtgag   1440
actcgtgatt gggactaagt cgtaacaagg                                    1470
```

<210> SEQ ID NO 2
<211> LENGTH: 1453
<212> TYPE: DNA
<213> ORGANISM: Bifidobacterium sp.

<400> SEQUENCE: 2

```
ggctcaggat gaacgctggc ggcgtgctta acacatgcaa gtcgaacggg atccgaggcg     60
cttgcgtctc ggtgagagtg gcgaacgggt gagtaatacg tgactaacct gcctcataca    120
tcggaatagc tcctggaaac gggtggtaat gccgaatgct ccaaccttcc gcatggatgg    180
ttgggaaagc gttagcggta tgagatgggg tcgcgtccta tcagcttgtt ggtggggtga    240
aggcccacca aggcttcgac gggtagccgg cctgagaggg tgaccggcca cattgggact    300
gagatacggc ccagactcct acggagcca gcagtgggga atattgcaca atgggcgaaa    360
gcctgatgca gcgacgccgc gtgcgggatg aaggccttcg ggttgtaaac cgcttttgat    420
tgggagcaag cgagagtgag tgtaccttc gaataagcac cggctaacta cgtgccagca    480
gccgcggtaa tacgtagggt gcaagcgtta tccggaatta ttgggcgtaa agagctcgta    540
ggcggtttgt cgcgtctggt gtgaaagtcc atcgcttaac ggtggatctg cccgggtac    600 gggcaggcta gagtgcgaca ggggagactg gaattcccgg tgtaacggtg aatgtgtag    660 atatcgggaa gaaccaccaat ggcgaaggca ggtctctggg tcgtcactga cgctgaggag    720
cgaaagcgtg gggagcgaac aggattagat accctgtag tccacgccgt aaacggtgga    780
tgctggatgt ggggcccatt ccacgggttc cgtgtcggag ctaacgcgtt aagcatcccg    840
cctggggagt acggccgcaa ggctaaaact caaagaaatt gacggggcc cgcacaagcg    900 gcggagcatg cggattaatt cgatgcaacg cgaagaacct tacctgggct tgacatgttc    960
```

```
ctgacggccg cggagacgcg gcttcccttc ggggcaggtt cacaggtggt gcatggtcgt    1020
cgtcagctcg tgtcgtgaga tgttgggtta agtcccgcaa cgagcgcaac cctcgccttg    1080
tgttgccagc acgttatggt gggaactcgc aagggaccgc cggggttaac tcggaggaag    1140
gtggggatga cgtcagatca tcatgcccct tacgtccagg gcttcacgca tgctacaatg    1200
gccggtacaa cgggatgcga cgcggtgacg cggagcggat cccttaaaac cggtctcagt    1260
tcggattgga gtctgcaact cgactccatg aaggcggagt cgctagtaat cgcgaatcag    1320
caacgtcgcg gtgaatgcgt tcccgggcct tgtacacacc gcccgtcaag tcatgaaagt    1380
gggtagcacc cgaagccggt ggcctaacct tttgggggga ccgtctaagg gtgagactcg    1440
tgattgggac taa                                                       1453

<210> SEQ ID NO 3
<211> LENGTH: 1467
<212> TYPE: DNA
<213> ORGANISM: Bifidobacterium sp.

<400> SEQUENCE: 3
gctcaggatg aacgctggcg gcgtgcttaa cacatgcaag tcgaacggga tccgaggcgc      60
ttgcgtctcg gtgagagtgg cgaacgggtg agtaatacgt gactaacctg cctcatacat     120
cggaatagct cctggaaacg ggtggtaatg ccgaatgctc caaccttccg catggatggt     180
tgggaaagcg ttagcggtat gagatggggt cgcgtcctat cagcttgttg gtggggtgaa     240
ggcccaccaa ggcttcgacg ggtagccggc ctgagagggt gaccggccac attgggactg     300
agatacggcc cagactccta cgggaggcag cagtgggaa tattgcacaa tgggcgaaag     360
cctgatgcag cgacgccgcg tgcgggatga aggccttcgg gttgtaaacc gcttttgatt     420
gggagcaagc gagagtgagt gtacctttcg aataagcacc ggctaactac gtgccagcag     480
ccgcggtaat acgtagggtg caagcgttat ccggaattat tgggcgtaaa gagctcgtag     540
gcggtttgtc gcgtctggtg tgaaagtcca tcgcttaacg gtggatctgc gccgggtacg     600
ggcaggctag agtgcgacag gggagactgg aattcccggt gtaacggtgg aatgtgtaga     660
tatcgggaag aacaccaatg gcgaaggcag gtctctgggt cgtcactgac gctgaggagc     720
gaaagcgtgg ggagcgaaca ggattagata ccctggtagt ccacgccgta acggtggat     780 gctggatgtg gggcccattc cacgggttcc gtgtcggagc taacgcgtta agcatcccgc     840
ctggggagta cggccgcaag gctaaaactc aaagaaattg acggggcccc gcacaagcgg     900
cggagcatgc ggattaattc gatgcaacgc gaagaacctt acctgggctt gacatgttcc     960
tgacggccgc ggagacgcgg cttcccttcg ggcaggttc acaggtggtg catggtcgtc    1020
gtcagctcgt gtcgtgagat gttgggttaa gtcccgcaac gagcgcaacc ctcgccttgt    1080
gttgccagca cgttatgtg ggaactcgca agggaccgcc ggggttaact cggaggaagg    1140 tgggggatgac gtcagatcat catgcccctt acgtccaggg cttcacgcat gctacaatgg    1200
ccggtacaac gggatgcgac gcggtgacgc ggagcggatc ccttaaaacc ggtctcagtt    1260
cggattggag tctgcaactc gactccatga aggcggagtc gctagtaatc gcgaatcagc    1320
aacgtcgcgg tgaatgcgtt cccgggcctt gtacacaccg cccgtcaagt catgaaagtg    1380
ggtagcaccc gaagccggtg gcctaacctt ttgggggga ccgtctaagg tgagactcgt    1440
gattgggact aaagtcgtaa acaaggt                                         1467

<210> SEQ ID NO 4
<211> LENGTH: 1452
```

```
<212> TYPE: DNA
<213> ORGANISM: Artificial
<220> FEATURE:
<223> OTHER INFORMATION: consensus sequence

<400> SEQUENCE: 4
gctcaggatg aacgctggcg gcgtgcttaa cacatgcaag tcgaacggga tccgaggcgc      60
ttgcgtctcg gtgagagtgg cgaacgggtg agtaatacgt gactaacctg cctcatacat     120
cggaatagct cctggaaacg ggtggtaatg ccgaatgctc aaccttccg catggatggt      180
tgggaaagcg ttagcggtat gagatggggt cgcgtcctat cagcttgttg gtggggtgaa     240
ggcccaccaa ggcttcgacg ggtagccggc ctgagagggt gaccggccac attgggactg     300
agatacggcc cagactccta cgggaggcag cagtggggaa tattgcacaa tgggcgaaag     360
cctgatgcag cgacgccgcg tgcgggatga aggccttcgg gttgtaaacc gcttttgatt     420
gggagcaagc gagagtgagt gtacctttcg aataagcacc ggctaactac gtgccagcag     480
ccgcggtaat acgtagggtg caagcgttat ccggaattat tgggcgtaaa gagctcgtag     540
gcggtttgtc gcgtctggtg tgaaagtcca tcgcttaacg gtggatctgc gccgggtacg     600
ggcaggctag agtgcgacag gggagactgg aattcccgt gtaacggtgg aatgtgtaga      660
tatcgggaag aacaccaatg gcgaaggcag gtctctgggt cgtcactgac gctgaggagc     720
gaaagcgtgg ggagcgaaca ggattagata ccctggtagt ccacgccgta acggtggat     780
gctggatgtg gggcccattc cacgggttcc gtgtcggagc taacgcgtta agcatcccgc     840
ctggggagta cggccgcaag gctaaaactc aaagaaattg acggggcccc gcacaagcgg     900
cggagcatgc ggattaattc gatgcaacgc gaagaacctt acctgggctt gacatgttcc     960
tgacggccgc ggagacgcgg cttcccttcg gggcaggttc acaggtggtg catggtcgtc    1020
gtcagctcgt gtcgtgagat gttgggttaa gtcccgcaac gagcgcaacc ctcgccttgt    1080
gttgccagca cgttatggtg ggaactcgca agggaccgcc ggggttaact cggaggaagg    1140
tggggatgac gtcagatcat catgcccctt acgtccaggg cttcacgcat gctacaatgg    1200
ccggtacaac gggatgcgac gcggtgacgc ggagcggatc ccttaaaacc ggtctcagtt    1260
cggattggag tctgcaactc gactccatga aggcggagtc gctagtaatc gcgaatcagc    1320
aacgtcgcgg tgaatgcgtt cccgggcctt gtacacaccg cccgtcaagt catgaaagtg    1380
ggtagcaccc gaagccggtg gcctaacctt ttgggggggag ccgtctaagg tgagactcgt    1440
gattgggact aa                                                        1452

<210> SEQ ID NO 5
<211> LENGTH: 212
<212> TYPE: DNA
<213> ORGANISM: Bifidobacterium sp.

<400> SEQUENCE: 5
tgcatgaggg tctgaagaac gtcgtggccg gatccaaccc gatcgcactg cgtcgcggtg      60
tcgagaaggc gtccgacgcc atcgtcaagg agctcgtcgc ctcggccaag gacgtggaaa     120
ccaaggagca gatcgcggct acggccacga tttccgccgc tgatcccgag gtcggcgaca     180
agatcgccga agcactcgac aaggtcggcc ag                                   212

<210> SEQ ID NO 6
<211> LENGTH: 17
<212> TYPE: DNA
<213> ORGANISM: Artificial
<220> FEATURE:
<223> OTHER INFORMATION: Primer
```

```
<400> SEQUENCE: 6
tccgacgcca tcgtcaa                                              17

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
cgatctgctc cttggtttcc                                           20

<210> SEQ ID NO 8
<211> LENGTH: 13
<212> TYPE: DNA
<213> ORGANISM: Artificial
<220> FEATURE:
<223> OTHER INFORMATION: Probe sequence

<400> SEQUENCE: 8
tcgtcgcctc ggc                                                  13
```